(12) United States Patent
Ancona et al.

(10) Patent No.: US 10,260,086 B2
(45) Date of Patent: Apr. 16, 2019

(54) QUANTUM DOTS IN MODULAR NUCLEIC ACID SCAFFOLDS OPERABLE AS NANOSCALE ENERGY HARVESTING AND FOCUSING ARRAYS

(71) Applicant: The United States of America, as represented by the Secretary of the Navy, Washington, DC (US)

(72) Inventors: Mario Ancona, Alexandria, VA (US); Ellen R. Goldman, Germantown, MD (US); Susan Buckhout-White, Silver Spring, MD (US); Igor L. Medintz, Springfield, VA (US); Joseph S. Melinger, Oakton, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/953,152

(22) Filed: Apr. 13, 2018

(65) Prior Publication Data
US 2018/0230522 A1 Aug. 16, 2018

Related U.S. Application Data

(62) Division of application No. 14/685,836, filed on Apr. 14, 2015, now Pat. No. 9,970,049.

(60) Provisional application No. 61/979,724, filed on Apr. 15, 2014.

(51) Int. Cl.
*C12Q 1/6818* (2018.01)
*G01N 21/64* (2006.01)

(52) U.S. Cl.
CPC ....... *C12Q 1/6818* (2013.01); *G01N 21/6428* (2013.01)

(58) Field of Classification Search
None
See application file for complete search history.

*Primary Examiner* — Kaijiang Zhang
(74) *Attorney, Agent, or Firm* — US Naval Research Laboratory; Roy Roberts

(57) ABSTRACT

The invention relates to a nanoscale antenna including a nucleic acid scaffold having a structure selected from the group consisting of a Holliday junction, a star, and a dendrimer; and a plurality of fluorophores attached to the scaffold and configured as a FRET cascade comprising at least three different types of fluorophores including at least one quantum dot, arranged with (a) a plurality of initial donor fluorophores fixed in exterior positions on the structure, (b) a terminal acceptor fluorophore fixed in a central position on the structure, and (c) a plurality of intermediate fluorophores fixed in positions on the scaffold between the initial acceptor fluorophores and the terminal acceptor fluorophores.

11 Claims, 12 Drawing Sheets
(12 of 12 Drawing Sheet(s) Filed in Color)
Specification includes a Sequence Listing.

Dendrimers
4-dye $0.5 \times R_0$

4:1

3:1

2:1

$0.5 \times R_0$

2:1

AF488    Cy5/AF647

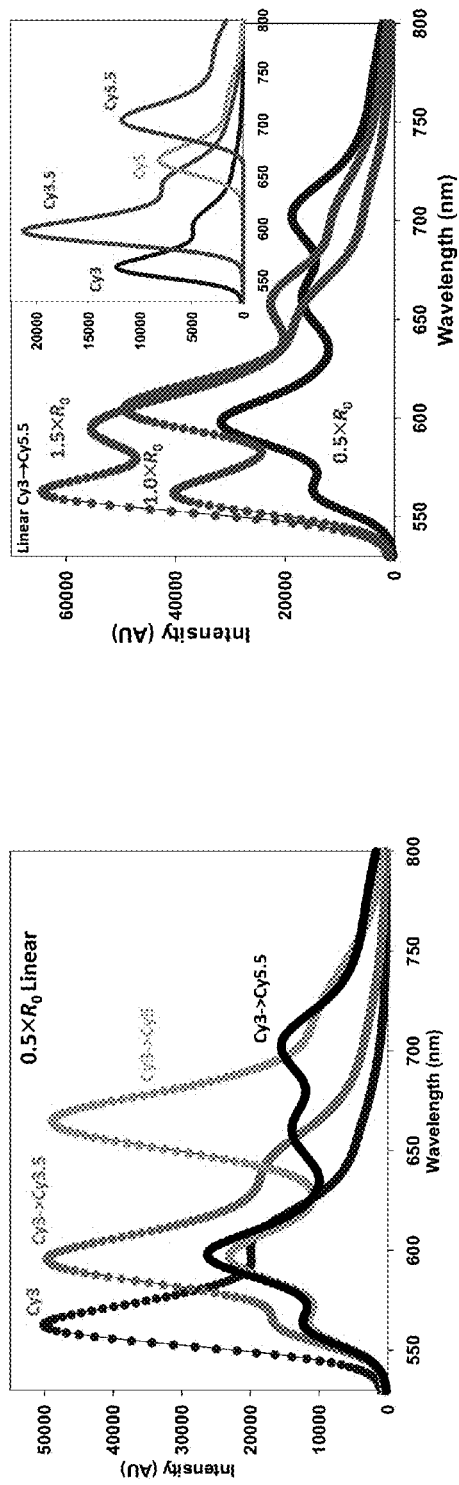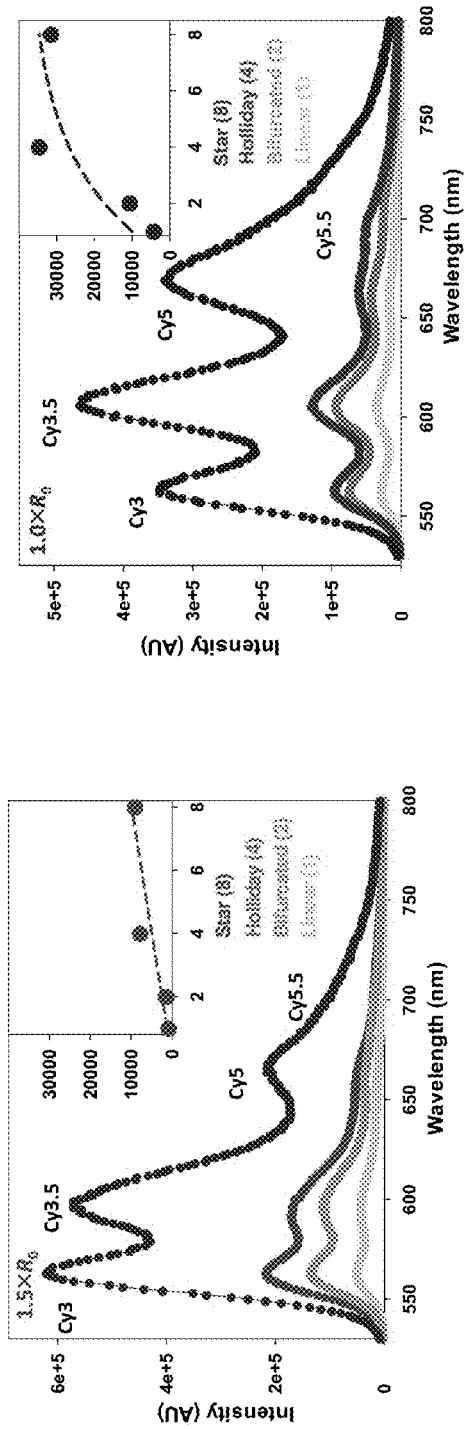
FIG. 3A
FIG. 3B
FIG. 3C
FIG. 3D

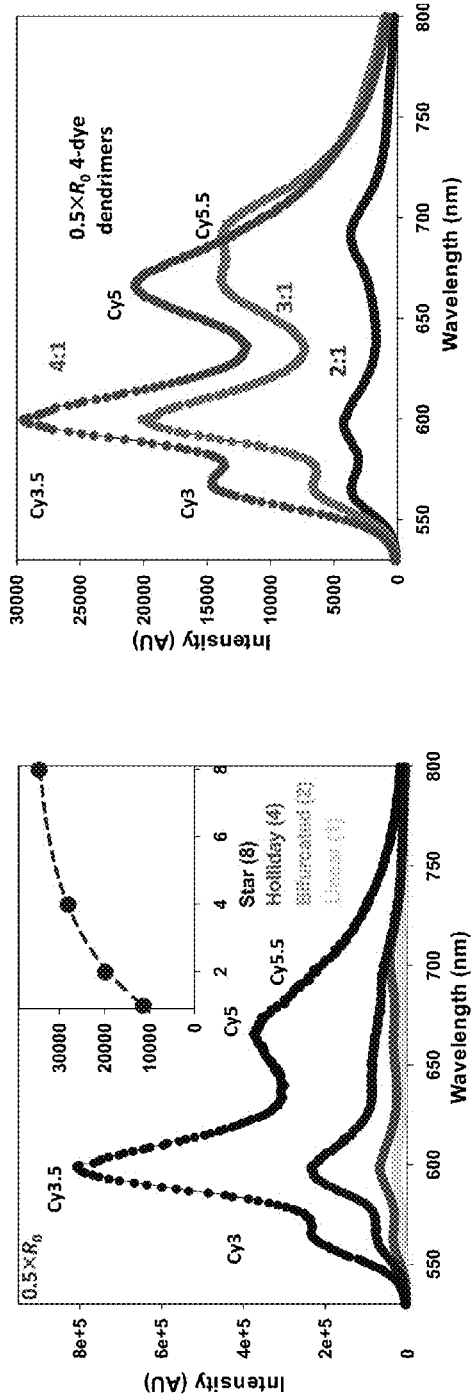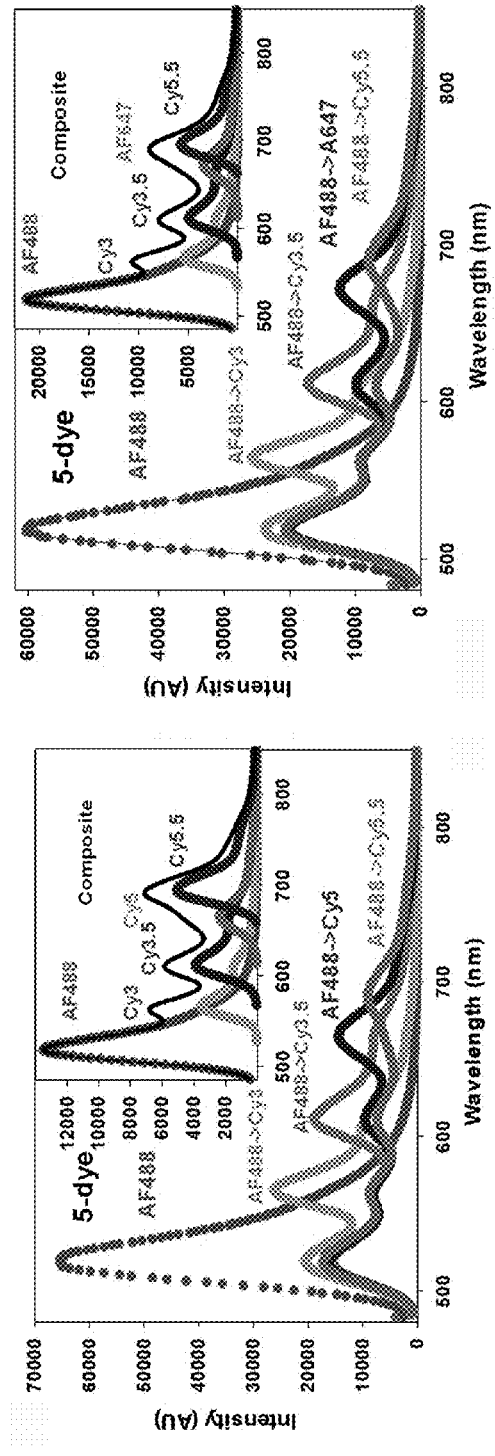
FIG. 3E
FIG. 3F
FIG. 3G
FIG. 3H

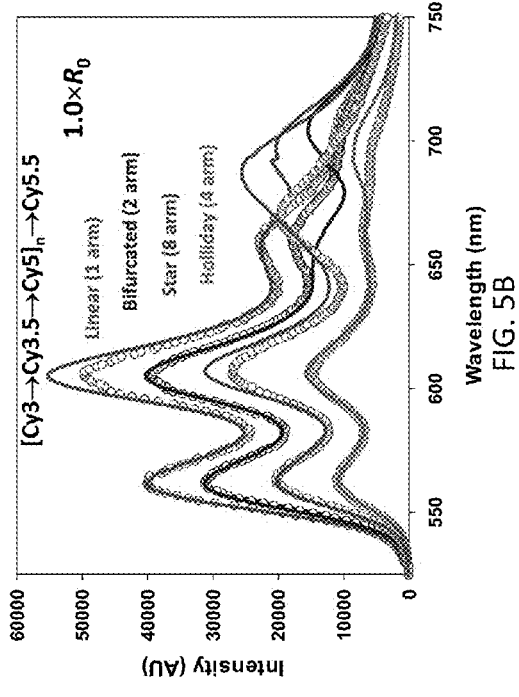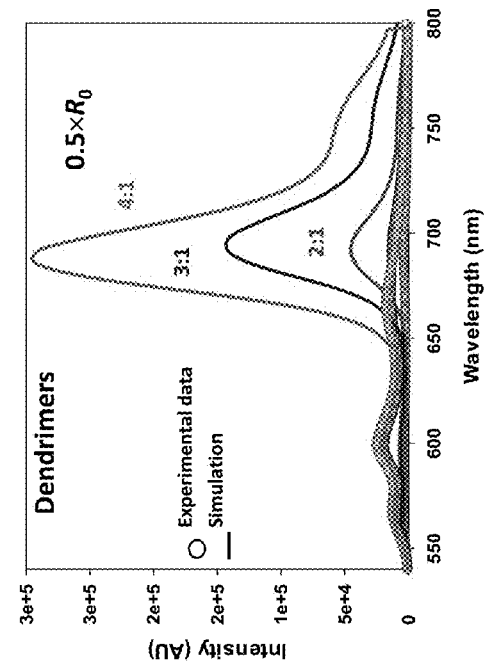
FIG. 5A
FIG. 5B
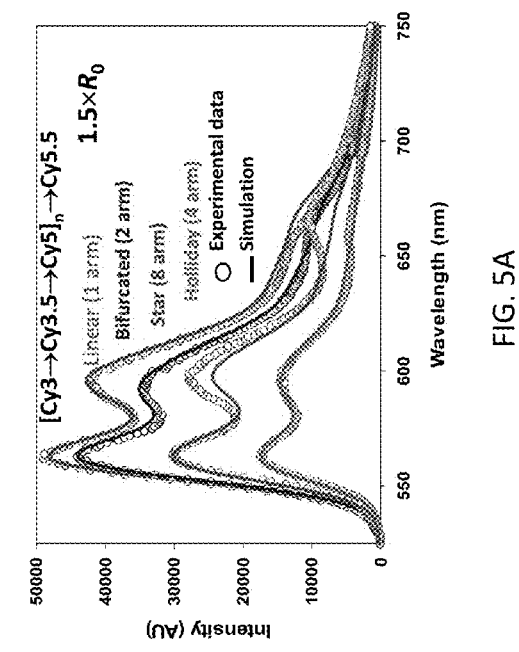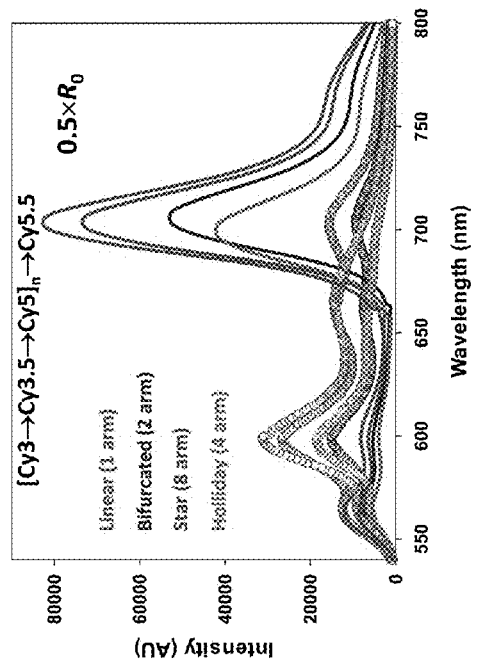
FIG. 5C
FIG. 5D

QUANTUM DOTS IN MODULAR NUCLEIC ACID SCAFFOLDS OPERABLE AS NANOSCALE ENERGY HARVESTING AND FOCUSING ARRAYS

CROSS-REFERENCE TO RELATED APPLICATIONS

This Application claims the benefit as a division of U.S. patent application Ser. No. 14/685,836 filed Apr. 14, 2015 which in turn claims the benefit of U.S. Provisional Application No. 61/979,727 filed on Apr. 15, 2014, the entirety of each of which is incorporated herein by reference.

BACKGROUND

A need exists for techniques to focus light excitonic energy and to study Förster resonance energy transfer (FRET) phenomena.

BRIEF SUMMARY

In a first embodiment, nanoscale antenna includes a nucleic acid scaffold having a structure selected from the group consisting of a Holliday junction, a star, and a dendrimer; and a plurality of fluorophores attached to the scaffold including at least one quantum dot and configured as a FRET cascade comprising at least three different types of fluorophores, arranged with (a) a plurality of initial donor fluorophores fixed in exterior positions on the structure, (b) a terminal acceptor fluorophore fixed in a central position on the structure, and (c) a plurality of intermediate fluorophores fixed in positions on the scaffold between the initial acceptor fluorophores and the terminal acceptor fluorophores.

In another embodiment, the scaffold of the nanoscale antenna of the first embodiment has a dendrimer structure.

In a further embodiment, a method includes exciting the antenna of the first embodiment with a light source.

In an additional embodiment, one or more portions of said scaffold incorporating intermediate fluorophores includes a toehold sequence, are detachable from the remaining portion of said scaffold upon contact with a sequence complementary to the toehold sequence.

Aspects of the invention, including details on techniques and additional exemplary DNA sequences, are described in Buckhout-White et al., "Assembling programmable FRET-based photonic networks using designer DNA scaffolds," Nature Communications 5, Article number:5615, doi: 10.1038/ncomms6615 and the associated supplementary material, the entirety of which is incorporated herein by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows 2-dye single FRET step system consisting of Cy3 donors paired to a Cy5 acceptor. The ratio of $Cy3_n$/Cy5 was incrementally increased using linear (n=1), bifurcated (n=2), Holliday junction (n=4), and star (n=8) structures. Donor-acceptor spacings are also varied for each as an increments of the Förster distance (0.75, 0.87, 1.0, 1.25, 1.5×$R_0$~54 Å). The 1.25×$R_0$ structures show dye locations relative to the DNA. FIG. 1B shows 4-dye, three FRET step system with sequential donor-acceptor arrangements of Cy3, Cy3.5, Cy5, Cy5.5 in photonic wire configurations. The number of [Cy3→Cy3.5→Cy5]$_n$ wires leading into each terminal Cy5.5 dye increases from 1 to 8 using linear, bifurcated, Holliday junction and 8-arm star constructs. The blue arrows show the directionality of the FRET cascade(s) in each structure. Donor-acceptor spacing varied here at 0.5, 1.0, 1.5×$R_0$. The 1.5×$R_0$ schematic shows the dye positions. FIG. 1C shows dendrimer-based FRET systems utilizing Cy3, Cy3.5, Cy5, Cy5.5 dyes in configurations were each dye preceding the central-terminal Cy5.5 has 2-, 3-, or 4-donors. Donor-acceptor spacings for the dendrimers were fixed at 0.5×$R_0$ and the 2:1 structures show dye locations. FIG. 1D shows dendrimer-based 5-dye FRET system utilizing AF488, Cy3, Cy3.5, Cy5, Cy5.5 dyes in configurations where each dye preceding the central-terminal Cy5.5 has 2-donors. An alternate version was assembled with AF647 replacing Cy5. Blue arrows schematically highlight the general donor-to-acceptor architecture. FIG. 1E shows normalized absorption/emission spectra for each of the dyes used. FIG. 1F plots the integrand of the J integral as a function of wavelength for pertinent donor-acceptor combinations.

FIG. 2A shows representative spectra excited at 515 nm showing the effect of altering Cy3-Cy5 donor acceptor spacing as a function of $R_0$~54 Å. The direct Cy3 only emission in each was used to normalize the data. FIG. 2B shows spectra from linear, bifurcated, Holliday junction and 8-arm star Cy3-Cy5 constructs where donor-acceptor spacing was maintained at ~0.75×$R_0$. Data were normalized to the Cy5 alone emission. FIG. 2C is a plot of the Cy5 terminal enhancement factor (TEF) as a function of the number of Cy3 donors/Cy5 acceptor for each of the donor-acceptor spacings as compared to the initial 1.5×$R_0$ $Cy3_1$→Cy5 system. Trend lines are added to aid the eye. FIG. 2D shows single pair FRET (spFRET) histograms for all 0.75×$R_0$ constructs, see SI for methodology. The number of FRET events for each curve has been normalized to 1. The green, blue and red, curves are shifted for presentation. Note the growth of the 0 FRET efficiency curve (representing a subpopulation that is not undergoing FRET) in the star structure and the shift to higher efficiency from linear to the star structure.

FIGS. 3A-3H illustrate exemplary 4-dye photonic wire and dendrimer systems. FIG. 3A illustrates representative data showing the spectral evolution of the 0.5×$R_0$ linear Cy3→Cy5.5 system as consecutive acceptor dyes are added to the initial Cy3 donor. FIG. 3B shows comparative spectral data for the 0.5, 1.0 and 1.5×$R_0$ linear systems. Data were normalized to the direct Cy5.5 emission at the same excitation. Inset, composite and deconvolved individual component spectra for the 0.5×$R_0$ linear system. FIGS. 3C-3E show spectra showing the FRET evolution of the (C) 1.5× $R_0$, (D) 1.0×$R_0$, and (E) 0.5×$R_0$ systems as the number of arms for each was increased from one to four. The inset in C-D pots the increase in Cy5.5 peak emission as a function of the number of arms all on the same scale. FIG. 3F shows comparative spectral data for the fully assembled 2:1, 3:1, and 4:1 0.5×$R_0$ dendrimer structures. Stoichiometry for 2:1 structure=$Cy3_8$→$Cy3.5_4$→$Cy5_2$→$Cy5.5_1$; 3:1 structure=$Cy3_{27}$→$Cy3.5_3$→$Cy5_3$→$Cy5.5_1$; 4:1 structure=$Cy3_{64}$→$Cy3.5_{16}$→$Cy5_4$→$Cy5.5_1$. Note all data in C—H were normalized to the direct Cy5.5 emission. Spectral data following the evolution of the $AF488_{16}$→$Cy3_8$→$Cy3.5_4$→$Cy5_2$→$Cy5.5_1$ (FIG. 3G) and AF488$_{16}$→Cy3$_8$→Cy3.5$_4$→AFF647$_2$→Cy5.5$_1$ (FIG. 3H) 2:1 dendrimer systems. Constructs with Cy3 initial dye were excited at 515 nm while those with AF488 were excited at 465 nm.

FIG. 4A is a plot of the Cy5.5 terminal enhancement factor (TEF) for the [Cy3→Cy3.5→Cy5]$_n$→Cy5.5 photonic wire and the 2:1, 3:1, and 4:1 0.5×R$_0$ dendrimer structures as compared to the initial 1.5×R$_0$ linear system. Note the break in vertical scale. FIG. 4B shows a comparison of the normalized emission profiles for the 0.5×R$_0$ 2:1 dendrimer and 8-arm photonic wire star structures. Dye ratios corresponding to each position in each structure are indicated with red or blue. Note the significant deconvolved Cy5.5 sensitization for the 2:1 dendrimer-inset. FIG. 4C is a comparative plot of the sensitized components at each step for the [Cy3→Cy3.5→Cy5]$_n$Cy5.5 photonic wire system. Dye emissions are scaled and normalized to the highest component, the Cy3.5 sensitized emission in the 8-arm star structure. FIG. 4D is a comparative plot of the sensitized components at each step for the 0.5×R$_0$ 2:1, 3:1, and 4:1 dendrimer system. Dye emissions are scaled and normalized to the highest component, the Cy3.5 sensitized emission in the 4:1 structure.

FIGS. 5A-5D show energy transfer analysis, namely a comparison of experimental data (circles) with spectra predicted by "ideal" simulation (lines) for 1-, 2-, 4-, and 8-arm multi-dye structures with dye spacings of (A) 1.5×R$_0$, (B) 1.0×R$_0$, and (C) 0.5×R$_0$, and (D) for dendrimers with dye spacing of 0.5×R$_0$ and branching ratios of 2:1, 3:1 and 4:1. In general, agreement between experiment and "ideal" simulation worsens as dye spacing gets smaller.

FIG. 6A shows the yield of target structures as assessed by gel electrophoresis or FPLC for multi-dye photonic wire structures and dendrimers with 0.5×R$_0$ dye spacing versus the number of arms or branching ratio, as compared with the corresponding yields derived from fitting the PL spectra when the structures are functionalized with either three or four dyes. FIG. 6B shows actual and ideal anywhere-to-end efficiency computed for the 4-dye linear structures as a function of the number of arms with the dye spacing as a parameter. FIG. 6C shows actual and ideal end-to-end efficiency computed for dendrimers as a function of branching ratio. Highlighting the importance of parallel FRET pathways, three ideal curves are shown, one assuming only nearest neighbor FRET (inset, left), one including only intra-arm FRET (inset, right), and one including all FRET processes (Ideal). FIG. 6D shows actual and ideal antenna gains as computed for the four-dye linear structures and dendrimers with 0.5×R$_0$ dye spacing. Note, the 0.5×R$_0$ linear photonic wire structure corresponds to the 1 arm dendrimer.

FIG. 7A is a schematic of a [[Cy3$_2$-Cy3.5]$_2$-Cy5]$_2$-Cy5.5 2:1 dendrimer where a toehold has been added onto the Cy3.5 containing oligonucleotide. FIG. 7B illustrates how, when exciting the initial Cy3 donor, this structure might efficiently direct exciton energy to the terminal Cy5.5 acceptor through multiple overlapping FRET pathways. Only the direct spectrally- and spatially-favored FRET pathways are shown here. FIG. 7C shows how the addition of the complimentary strand to the structure in FIG. 7A (in a room temperature isothermal transition) removes the Cy3.5 labeled strands from the structure. FIG. 7D shows that this results in a significant decrease in the amount of excitonic energy being delivered to the Cy5.5 terminal acceptor along with the magnitude of its signal—even when excited at the Cy5 donor preceding it.

FIG. 8A shows the antenna effect (AE) derived by comparing the emission of the terminal Cy5.5 when the system is excited at the initial Cy3 donor (515 nm) as compared to exciting the Cy5 donor (635 nm) preceding the Cy5.5. This is described as AE=Cy5.5 PL(exc. 515)/=Cy5.5 PL (exc. 635). This signal enhancement reflects how much more the Cy5.5 is emitting when the system is excited at the outer Cy3 dyes (n=8) than at the Cy5 dyes (n=2) preceding the Cy5.5 acceptor. In this case it is around 2.5 times more. Addition of the complement, which removes the Cy3.5 intermediary, decreases this signal enhancement significantly. This directly shows how much more Cy5.5 signal and change in signal is available for a potential sensing event using the DNA antenna to sensitize the terminal acceptor. FIG. 8B shows the initial Cy3 and terminal Cy5.5 deconvoluted signal in the full structure when excited at 515 nm (Cy3) and after removing the Cy3.5 intermediary. Note the relative changes in emission and emission ratios which would be directly available to enhance the available signal and change in signal for a biosensing event.

DETAILED DESCRIPTION

Definitions

Figure 1A:
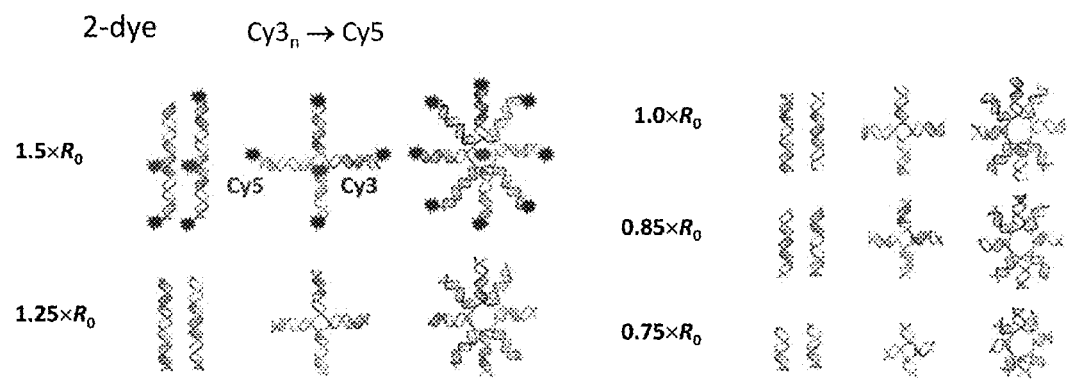
FIGS. 1A-1F depict exemplary DNA structures and fluorophore photophysical properties.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Described herein is a technique for the modular assembly of energy transfer moieties (namely fluorophores such as fluorescent dyes) into a nanoscale antenna such that energy (light) is absorbed at some discrete point(s) and funneled in a specific direction, such as inward and/or outward from a central point via Förster resonance energy transfer (FRET).

The fluorophores are fixed in positions on a nucleic acid scaffold, for example a modular scaffold, preferably a DNA scaffold comprising oligonucleotide elements that assemble on the basis of nucleic acid complementarity.

Some embodiments have a single terminal acceptor fluorophore, however trials with more than one terminal acceptor flurophore were found to increase the overall energy transfer efficiency through the system. Multiple terminal acceptors increase the probability that the exciton will be transferred to the terminal dye(s), especially if the energy is being funneled through multiple pathways.

More than simple linear arrangements, this technique utilizes multi-fluorescent molecular configurations in such a way that energy is transferred though multiple, discrete steps as desired. Furthermore, the arrangement of these molecules and the number of steps involved can be quickly modified through inclusion or exclusion of specific DNA strands allowing for many different permutations to be created within one sample set. Fundamental to the activity of these structures, termed nanoscale antennas, is the ability to harvest light energy and then concentrate it or focus/direct it in a particular direction. It is expected that such nanoscale antennas could be incorporated into active nanodevices to provide power or other functionalities.

Excitation of a nanoscale antenna may occur using a instrument, for example with a laser, or otherwise. For example, it may operate following chemical excitation such as that of bioluminescent resonance energy transfer (BRET) where an enzyme such as luciferase chemically generates the light from oxidizing substrate. Alternately, the antenna may operate on the basis chemically generated light.

Suitable fluorophores can by site-specifically fixed to the nucleic acid, preferably by covalent attachment. Possible modes of attachment for fluorophores include using (a) phosphoramidite chemistry, with dyes inserted directly into the scaffold by end-labeling or by placing them between two bases and opposite, for example, an unpaired A base; (b) succinimidyl ester chemistry, e.g., by attachment to an amine-modified linker placed either 5', 3' or inserted internally; (c) maleimide thiol chemistry; (d) carboxyl-amine amide bond formation by carbodiimide chemistry; (e) azide-alkyne cycloaddition; and (f) electrostatic binding, as well as combinations thereof. Other suitable attachment mechanisms can be contemplated by one of skill in the art.

The demonstrated structures vary the distance between the fluorophores according to their Förster resonance energy transfer (FRET) distance (where $R_0$ denotes the Förster distance which is the distance where 50% FRET efficiency occurs). The distances between fluorophores can be controlled as desired when designing the scaffold.

Various types of structures were designed, assembled, tested and analyzed. The first of these structure types, the 2-dye system, aimed to isolate the effect of the multiple donors separate from the multiple-dye cascading FRET. For this system, a well-characterized Cy3-Cy5 donor acceptor pair was used. In an effort to understand the potential trends seen by increasing the number of donor with reference to a single acceptor, the system assembled dyes according to a $D_n$-A formula, where n=1, 2, 4 or 8 and where each D individually represents a fluorophore donor and where A represents an acceptor, with all the D fluorophores apart from D1 also operable as intermediate donor/acceptors. This led to the creation of a unidirectional linear structure, a bifurcated linear structure, an intersecting structure based on a Holliday junction and an 8-armed star structure. These structures represent a truly modular system in that all versions within a given distance were made using the same set of 10 strands of DNA.

The linear and bifurcated structures are made from a simple double stranded piece of DNA. The Cy5 dye is internally labeled at the center of one of the oligos and the 3', for the linear structures—3' and 5' ends for the bifurcated are labeled with a Cy3. For the Holliday structure, an internally labeled Cy5 is placed on the center of one of four single-stranded oligos. Two of the three remaining oligos are labeled at both the 3' and 5' ends with Cy3 and a fourth oligo is unlabeled. The star is constructed similarly to the Holliday structure with a central, internally labeled Cy5, 4 double Cy3-labeled strands and 3-unlabeled strands. A variety of spacing were investigated including 0.75-, 0.87-, 1.0-, 1.25- and 1.5×$R_0$. This was accomplished by changing the length of the DNA arms.

Exemplary oligonucleotide elements used to create these structures at the 1.5×$R_0$ spacing are as follows, where an asterisk "*" represents the location of a nucleotide modification to incorporate a dye:

T1 (SEQ ID No: 1; 5' Cy3, 3' Cy3)
*GGAGAGATGGTTCAGCCGCAATCCTCGCCTGCACTCTACCTGACTTC
C*

T2 (SEQ ID No: 3; Internal Cy5)
GGAAGTCAGGTAGAGTGCAGGCGA*GAGCACGAGTCTTGCTGCTTAGC T3 (SEQ ID No 3; 5' Cy3, 3' Cy3)
*GCTAAGCAGCAAGACTCGTGCTCACCGAATGCCACCACGCTCCGTCG
C*

T4 (SEQ ID No: 4)
GCGACGGAGCGTGGTGGCATTCGGCGTCCAGCTCTGATCCAATACTCC

T5 (SEQ ID No: 5; 5' Cy3, 3' Cy3)
*GGAGTATTGGATCAGAGCTGGACGACAATGACGTAGGTCCTAACCTC
C*

T6 (SEQ ID No 6):
GGAGGTTAGGACCTACGTCATTGTACTATGGCACACATCCCTAGTTCC

T7 (SEQ ID No: 7; 5' Cy3, 3' Cy3)
*GGAACTAGGGATGTGTGCCATAGTGGTCAACGCATACACCTTCTATC
C*

T8 (SEQ ID No: 8)
GGATAGAAGGTGTATGCGTTGACCGGATTGCGGCTGAACCATCTCTCC

T9 (SEQ ID No: 9)
GCGACGGAGCGTGGTGGCATTCGGGGATTGCGGCTGAACCATCTCTCC

T10 (SEQ ID No: 10; Internal Cy5)
GGAGGTTAGGACCTACGTCATTG*CGTCCAGCTCTGATCCAATACTCC The "eight way" star structure eight sequences T1-T8. The "four-way" Holliday star used T1, T2, T3, and T9. The linear structures used T5 and T10.

Moving to a more complex 4-dye system expands to include the four sequentially arrayed dye cascade of Cy3, Cy3.5, Cy5 and Cy5.5. This system is designed to assemble the dyes similar to the 2-dye system above in a $D1_n$-$D2_n$-$D3_n$-A, where n equals 1, 2, 4, or 8 and where each D individually represents a fluorophore donor and where A represents an acceptor, with all the D fluorophores apart from D1 also operable as intermediate donor/acceptors. These structures are measured at three different Förster distances (0.5-, 1.0- and 1.5×$R_0$). The 1.0- and 1.5×$R_0$ spacing structures are designed much the way of the 2-dye systems. To account for the additional space needed for the cascading FRET dyes, one side of the double stranded arm is extended. This occurs on the linear and bifurcated structures and on each arm of the Holliday and star structures. The extended arms then act as a template for the smaller dye-labeled oligos to be assembled. Given the close distances needed in the 0.5×$R_0$ spacing, the assembly proceeds differently. For the linear structure, 4 strands concatenate together to form the structure and each of these strands contains one dye. The bifurcated structure also uses concatenated strands but requires the Cy5 to be double-labeled and one of the oligos to be double-labeled with Cy3 on the 3' end and Cy5.5 on the 5' end. All other oligos contain one dye at either end or internally-labeled. The Holliday and star structures contain an internal Cy5.5 at the center junction. Two of the remaining central oligos in the Holliday and four for the star contain double internally labeled Cy5 dyes. The Cy3 and Cy3.5 are assembled similar to the 1-way structures in a concatenated manner at the end of the central oligos.

In the 4-dye system, the first three dyes engage in a 1:1 correspondence. Another set of DNA structures described here aimed to create a system where each acceptor has multiple donors according to the following: $D1_n^3$-$D2_n^2$-$D3_n$-A, where n equals 2, 3, or 4 and where each D individually represents a fluorophore donor and where A represents an acceptor, with all the D fluorophores apart from D1 also operable as intermediate donor/acceptors. In order to facilitate this type of structure an exponential branching motif is used. The dendrimer system in the center begins with a branch of n arms and then each subsequent branch contains n+1 arms. The structures are designed with 2 long 58 base oligos, one of which is internally labeled at the center with Cy5.5 and the other has 2 internal Cy5 labels that occur at the branching junction. 40 base oligos are assembled to the 58 base center and are double, internally-labeled with Cy3.5. Finally the ends are 18 base oligos with 3' and 5' labeled Cy3.

Spectral Overlap

Figure 1B:
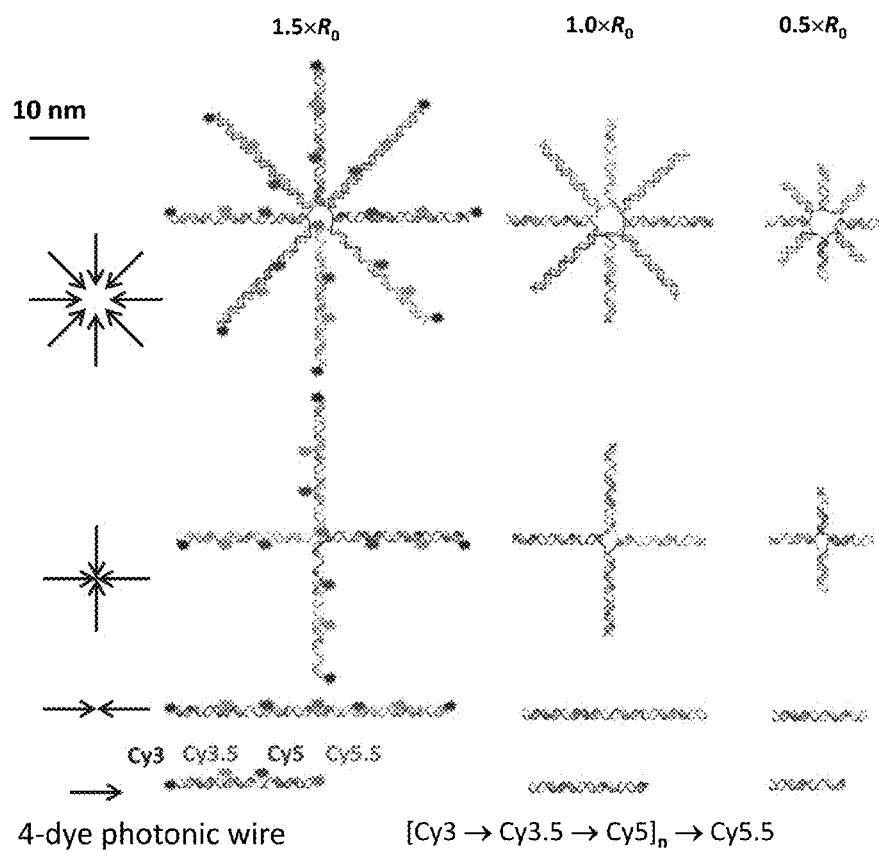
Figure 1C:
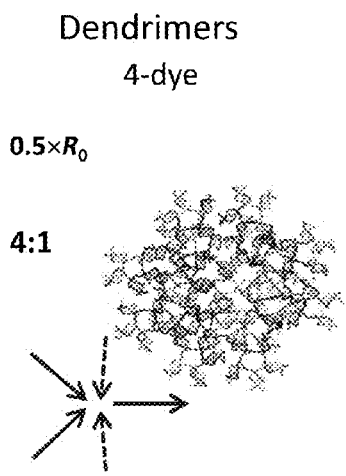
Figure 1C:
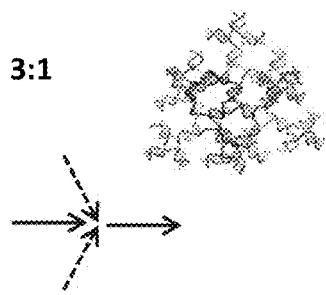
Figure 1C:
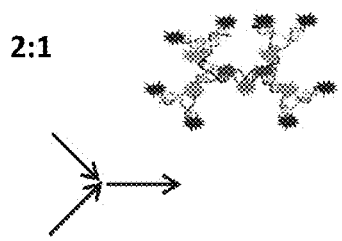
Figure 1D:
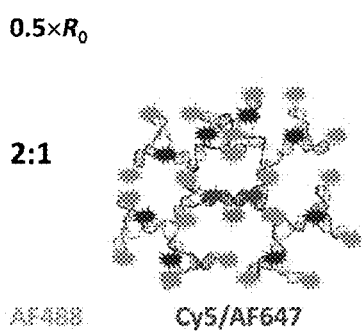
Figure 1E:
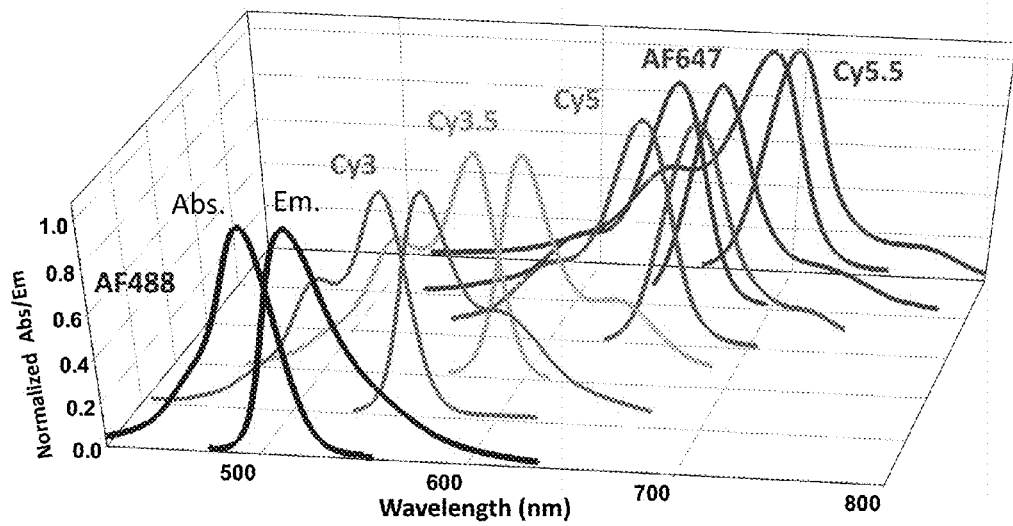
Figure 1F:
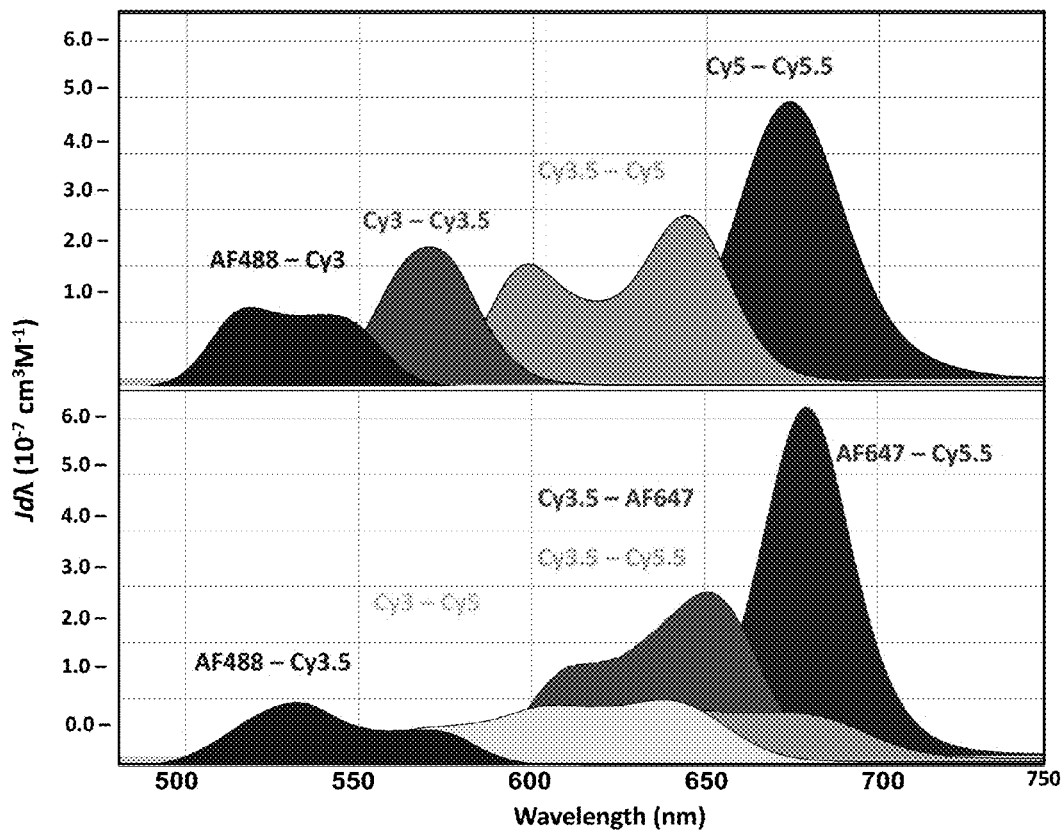

The particular cyanine and Alexa Fluor dyes were chosen for study in part because they are commercially available site-specifically attached (internal or terminal) to DNA. In addition, most have been used previously in photonic wire work, thereby providing archival background on their performance. The plot in FIG. 1E shows the dye absorption/emission spectra and highlights the potential of this system to be excited at ~515-550 nm for Cy3, and then to transfer exciton energy in 1-step to Cy5 or in a 3-step FRET cascade to the terminal Cy5.5. Alternatively, the AF488 can be excited at 460-490 nm and transfer energy in a 4-step cascade to Cy5.5. Relevant photophysical parameters are listed in Table I along with the calculated spectral overlap integrals (J) and $R_0$ for each donor-acceptor pair. $R_0$ values for each FRET pair varied between ~40 to 70 Å while J varied almost an order of magnitude from $9.4\times10^{-13}$ to $1.2\times10^{-12}$ cm$^3$M$^{-1}$. Values for potential homoFRET between like dyes are also listed. Plots of the integrand for the J integral as a function of wavelength for pertinent donor-acceptor pairs are shown in FIG. 1F and reinforce the concept of transferring exciton energy sequentially over a ~250 nm portion of the spectrum using multiple ET steps. The sequential nature of the system suggests that longer-range FRET, i.e. skipping over an intermediary dye, is not as favorable.

Photophysical Performance $Cy3_n \rightarrow Cy5$ Single FRET Step Systems

Figure 2A:
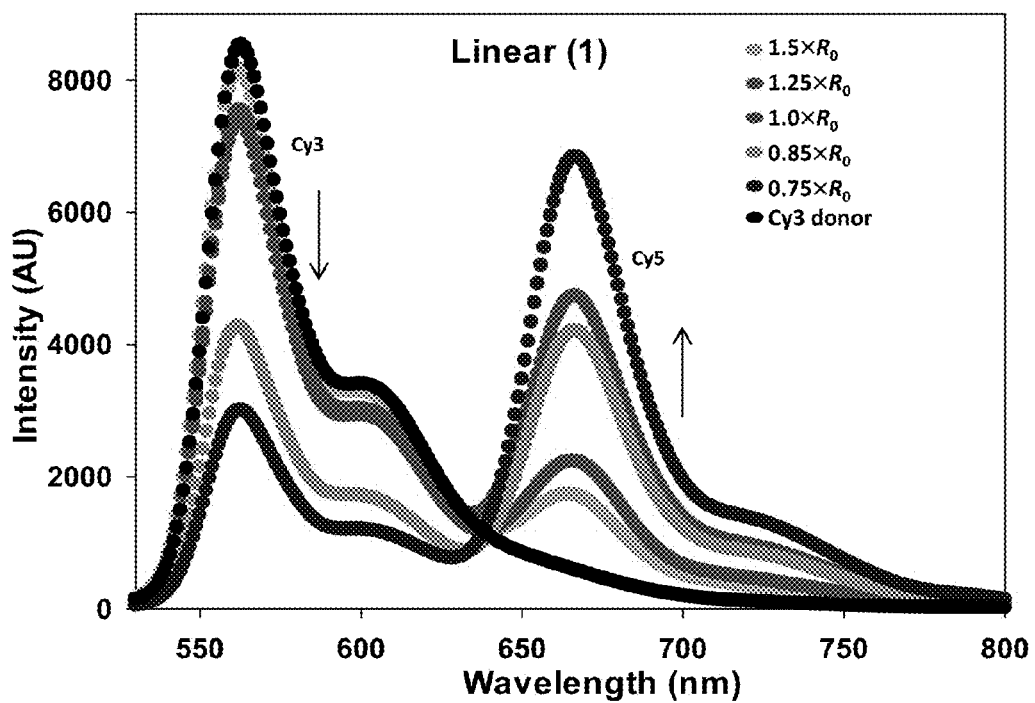
FIGS. 2A-2D illustrate exemplary single FRET systems using 2 dyes.
Figure 2B:
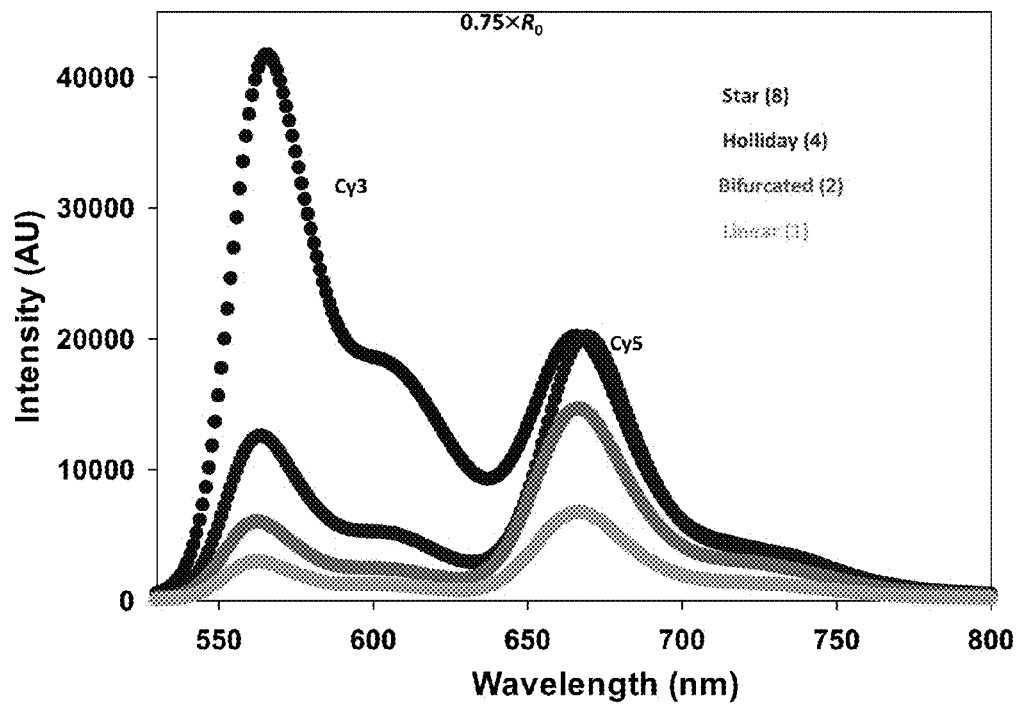

This system was designed to evaluate the sensitization of a single acceptor as function of the number of donating dyes and how this depends on the separation distance. For these experiments, the DNA scaffold was used to array 1, 2, 4, or 8 Cy3 donors around a central Cy5 acceptor at separation distances ranging from 0.75-1.5×$R_0$ (~40-81 Å). Samples were prepared and emission spectra collected with 515 nm excitation. FIG. 2A shows representative, normalized spectra collected from the linear ($Cy3_1 \rightarrow Cy5$) system as the fluorophore distances were varied in comparison to Cy3 alone. As expected, the Cy3 donor emission decreases and the corresponding Cy5 acceptor sensitization increases as a function of decreasing separation. FIG. 2B presents normalized spectra from the closest 0.75×$R_0$ assemblies as the ratio of Cy3 to Cy5 increases. Direct Cy3 emission increases concomitant with its valence and Cy5 sensitization also increases but appears to plateau.

Terminal enhancement factor (TEF), antenna effect (AE), and exciton end-to-end efficiency (E) are the metrics applied to characterizing the energy harvesting/sensitizing capabilities in these systems. The end-to-end energy transfer efficiency, E, of each construct was calculated using the expression:

$$E=[(\Phi_{AD}-\Phi_A)/Q_A]/(\Phi_D/Q_D)$$

where $\Phi_{AD}$ is the integrated PL area of the terminal acceptor in the presence of donor, $\Phi_A$ is the integrated PL area of the terminal acceptor in the absence of donor, $\Phi_D$ is the integrated PL area of the donor in the absence of acceptor, and $Q_A$ and $Q_D$ is the quantum yield (QY) of the terminal acceptor and donor, respectively. The value E provides a means to assess the terminal acceptor re-emission following sensitization from an upstream fluorophore while also accounting for the QY of the initial donor and terminal acceptor. The values of $\Phi_D$ and $\Phi_A$ were determined by numerical integration of PL area fits from molar equivalent samples containing only the donor or acceptor of interest, respectively. The value $\Phi_{AD}$ was determined by deconvolution of the composite emission spectrum of a FRET construct into the PL intensity from each contributing fluorophore and numerical integration in the manner described above. The end result was a series of PL intensity curves corresponding to each fluorophore within a FRET construct. The value $\Phi_{AD}$ is the integrated PL intensity of the terminal acceptor in the presence of the primary FRET donor.

In constructs possessing multiple donors, E accounts for energy that has entered the system through the initial donor as well as from direct excitation of intermediate fluorophores serving as donors. For example, in the full Cy3-Cy3.5-Cy5-Cy5.5 construct the majority of energy is introduced to the system via direct excitation of Cy3. However, some energy is introduced through direct excitation of Cy3.5 and to a lesser extent Cy5. Therefore, the magnitude of E reflects the amount of terminal acceptor sensitization arising from energy that has entered the system through any upstream fluorophore, of which the Cy3 emission provides the significant majority.

Similar analysis was employed to quantify the average FRET donor efficiency, $E_D$, and acceptor re-emission efficiency, $E_A$, for each donor-acceptor pair within a particular construct. Direct excitation spectra fits for each fluorophore (determined from molar equivalent control samples) were subtracted from fit emission data sets to minimize contributions to the composite PL intensity arising from direct excitation of fluorophores subsequent to the initial donor. Following the scaling/subtraction method outlined above, the resulting spectra were deconvoluted to determine the contributions from the primary donor emission and the sensitized acceptor contribution in a particular configuration. These deconvoluted data were numerically integrated and used to calculate $E_D$ and $E_A$ for each donor-acceptor conjugate:

$$E_D=1-F_{DA}/F_D$$

and $$E_A=F_{AD}/F_D$$

where $F_{DA}$ is the integrated PL area of the donor is the presence of acceptor, $F_D$ is the integrated PL area of the donor is the absence of acceptor, and $F_{AD}$ is the integrated PL area of the acceptor in the presence of donor. The value $E_D$ and $E_A$ represent the donor loss and acceptor sensitization, respectively. In constructs with multiple fluorophores, the efficiency for each donor-acceptor pair is analyzed as an independent step, regardless of whether the donor was directly excited and/or sensitized.

The antennae effect (AE) was measured for all systems and is defined here as:

$$AE_{Cy3 \rightarrow Cy5} = I_{Cy5,515\ nm} / I_{Cy5,635\ nm}$$

or $$AE_{Cy3 \rightarrow Cy3.5 \rightarrow Cy5 \rightarrow Cy5.5} = I_{Cy5.5,515\ nm} / I_{Cy5.5,685\ nm}$$

where $I_{Cy5,515\ nm}$, $I_{Cy5,635\ nm}$ and $I_{Cy5.5,515\ nm}$, $I_{Cy5.5,685\ nm}$ are the fluorescence intensities (deconvolved area under the curve) of the terminal Cy5 or Cy5.5 following excitation of the initial Cy3 donor at 515 nm and direct excitation at 650/700 nm, respectively.

The terminal enhancement factor (TEF) was introduced to allow for a comparison of the PL intensity of a terminal acceptor (Cy5 or Cy5.5) across all FRET constructs (linear, bifurcated, Holliday junction, 8-arm star and dendrimers). First, PL data were normalized using the intensity of the Cy3-DNA conjugate since molar equivalence was maintained across all data sets. This accounted for any instrument variation during data collection. The intensity from the unidirectional $0.5 \times R_0$ construct was chosen as unity and all other data scaled accordingly. A second scaling factor was then introduced to account for presumptive number of active Cy3 dyes within a particular construct: 1 for linear, 2 for the bifurcated, 4 for the Holliday junction, 8 for the 8-arm star way linear and 2:1 dendrimer, 27 for the 3:1 dendrimer, and 64 for the 4:1 dendrimer. The PL intensity of terminal acceptor, determined from deconvolution of composite spectra, was subjected to this normalization and scaling procedure and tabulated. The terminal PL intensity with the lowest value (unidirectional, $1.5 \times R_0$) was then set to unity and all other data scaled up by this value. The result is a series of normalized data points reporting the PL intensity of Cy5.5 in the full Cy3-Cy3.5-Cy5-Cy5.5 configuration while also accounting for the various linear and dendrimeric constructs. Enhancement of sensitization in different experimental constructs is then given in comparison to an initial construct. TEF is applied across structures containing a single or equivalent terminal acceptor dye regardless of donor number, configuration or donor-acceptor separation.

Figure 2C:
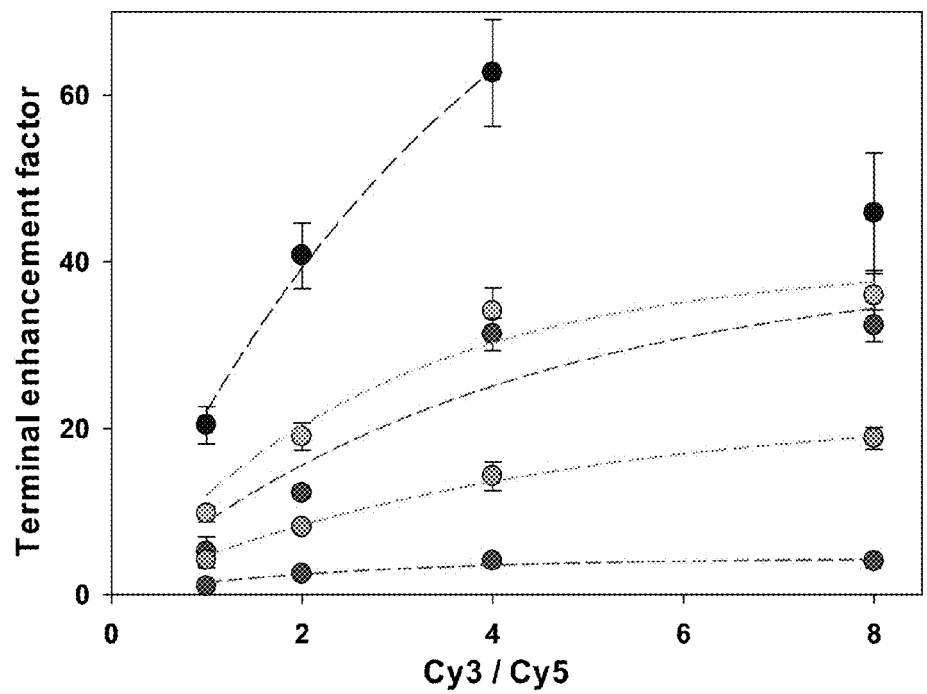
Figure 2D:
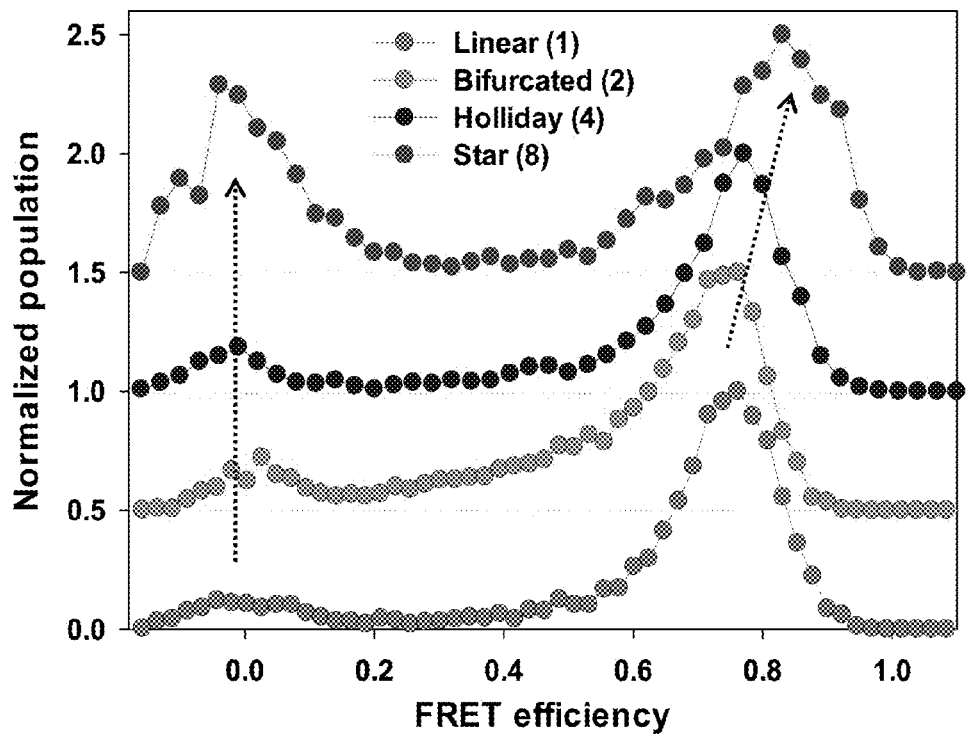

Loosely speaking, both TEF and AE are relative measures of performance, giving the degree of enhancements over either a "reference" system (TEF) or direct excitation of the terminal dye (AE), while E estimates the efficiency of exciton delivery. Each can be measured empirically, directly from experiment, or calculated as theoretical values. FIG. 2C plots TEF as a function of the number of Cy3 donors per Cy5 acceptor for each of the donor-acceptor spacings where the "reference" system is the Cy5 sensitization of the $1.5 \times R_0$ linear construct. The plot shows that output can be magnified by >60 times by decreasing the inter-fluorophore separation to $0.75 \times R_0$ and increasing the number of donors to four. Regarding the corresponding AE and E metrics given in Table 2, the $0.75 \times R_0$ Holliday junction manifests the best AE at nearly 300% while the $0.75 \times R_0$ bifurcated system achieves ≥50% E. Excepting the $0.75 \times R_0$ structures, AE generally increases with Cy3 donor number, while E values are relatively constant up to a ratio of 4 and then decrease in going from 4 to 8.

$[Cy3 \rightarrow Cy3.5 \rightarrow Cy5]_n \rightarrow Cy5.5$ Photonic Wires

This system is a generalization of the two-dye system of the previous sub-section into an antenna with more dyes, a larger collection area, and perhaps higher performance. FIG. 3A shows the spectral evolution of the $0.5 \times R_0$ linear (photonic wire) system as consecutive acceptor dyes are added to an initial Cy3 donor. A clear loss of donor emission and a concurrent sensitization of each acceptor dye are noted for each added step. FIG. 3B compares normalized spectra from the 1.5, 1.0, and $0.5 \times R_0$ linear Cy3→Cy5.5 systems confirming that closer dye spacings significantly improve FRET efficiency as expected. The data presented in FIGS. 3C-E correspond to assembling the initial [Cy3→Cy3.5→Cy5] portion as linear photonic wires with inter-dye spacings of 1.5, 1.0, and $0.5 \times R_0$ and compare the increase in wire valency from one to eight around the terminal Cy5.5, see FIG. 1B for structure. The data are all normalized to the direct Cy5.5 excitation component and have the Cy3.5, Cy5 and Cy5.5 direct excitation components removed to emphasize the resulting sensitization. Only the $1.0 \times R_0$ Holliday/star and $0.5 \times R_0$ constructs manifest any significant Cy5.5 sensitization. It is also clear from these plots that the DNA accurately controls the spacing of these 4 dyes and that the net effect of spacing propagates easily through the 3 step FRET transfer.

Interestingly, subtracting the directly excited Cy3.5 component in the $0.5 \times R_0$ bifurcated structure with all 4 dyes present removes all of its detected emission, suggesting that it is executing energy transfer that is perfect to the limits of measurement. The $0.5 \times R_0$ bifurcated system also shows the best AE with a value approaching 300% in Table III. The AE and E metrics for this data (Table III) also reflect the better performance of the $0.5 \times R_0$ construct, while the TEF (FIG. 4A) shows a similar overall pattern reminiscent of the single FRET step plots in FIG. 2C. Most interesting is that the efficiency is roughly the same irrespective of the number of arms, indicating that arms act as independent photonic wires without appreciable exciton transfers between them. Finally, these data show that the sensitization of the terminal acceptor can still be enhanced by at least 30-40× despite three intervening FRET steps if the number of donor wires and their geometric arrangement are optimized.

In a further generalization of the star antennae geometry, add additional levels of branching were added as dendrimeric systems. These begin to have densities of chromophores that are reminiscent of natural light-harvesting complexes. $[[Cy3_n \rightarrow Cy3.5]_n \rightarrow Cy5]_n \rightarrow Cy5.5$ dendrimeric DNA scaffolds were designed such that each dye preceding the Cy5.5 was sensitized by either of 2:1, 3:1, or 4:1 donors:acceptor, and with dye spacings maintained at $0.5 \times R_0$ for high efficiency. This short inter-dye requirement resulted in structures that grew in complexity and density with initial ratios of Cy3:Cy5.5 donor ratios growing exponentially from 8 to 27 to then 64 as shown in FIG. 1C. FIG. 3F compares normalized spectra (with the direct excitation components subtracted) as collected from the final dendrimer structures assembled with all dyes present. The spectral profiles tend to be bimodal with initial Cy3 emission increasing with valence and a minimal contribution of Cy3.5 emission in the 2:1 and 4:1 structures. The sensitized Cy5.5 component also appears to be most prominent in the 3:1 assembly with an AE value approaching 400% and the highest E value of the three at 23% (Table III). Here, we estimate formation efficiency at 58%, 84% and 66% for the 2:1, 3:1, and 4:1 structures, respectively, based on FPLC analysis (SI) and attribute any deficiencies in formation to the complexity of the designs.

The 2:1 dendrimer design was extended by adding an initial AF488 dye donor to create an [[AF488$_n$→Cy3]$_n$→Cy3.5]$_n$→Cy5/AF647]$_n$→Cy5.5 construct and assembled two variants with either Cy5 or AF647 present in the penultimate step. FIGS. 3G and 3H show spectra collected from the final dendrimer structures assembled with all dyes present. Despite the added FRET step, E values are comparable to the previous dendrimers at 19% (Cy5 construct) and 16% (AF647) while AE yields are 180% and 140%, respectively.

Figure 4A:
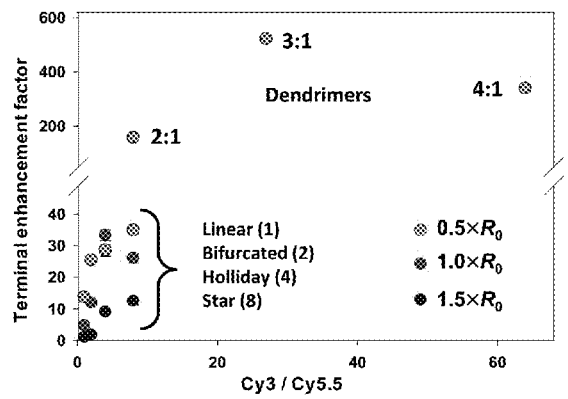
FIGS. 4A-4D show energy transfer in the photonic wire and dendrimer systems.
Figure 4B:
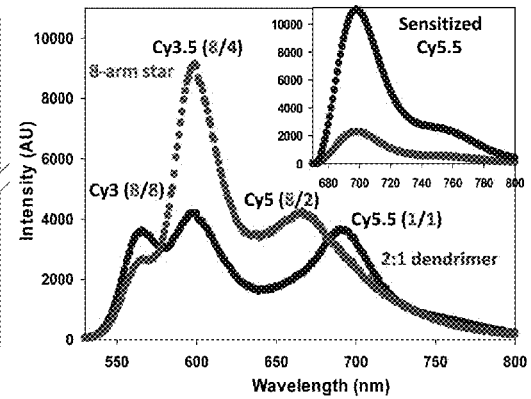
Figure 4C:
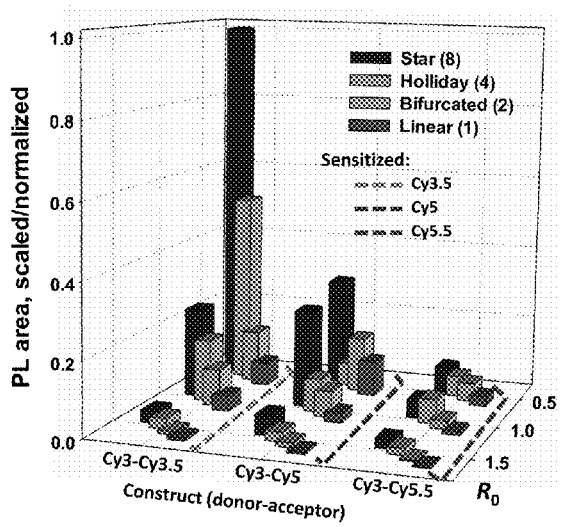
Figure 4D:
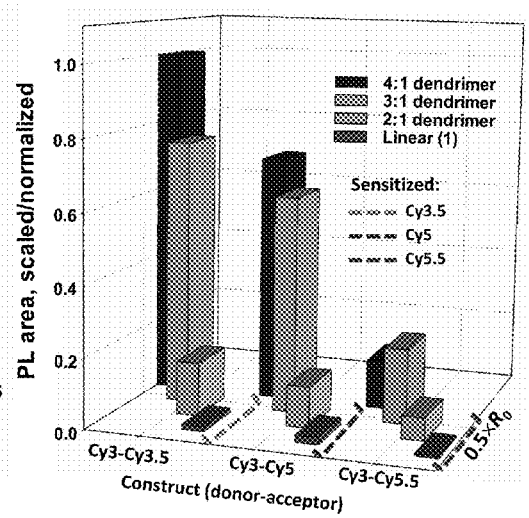

FIGS. 4A-4D show energy transfer in the photonic wire and dendrimer systems. FIG. 4A is a plot of the Cy5.5 terminal enhancement factor (TEF) for the [Cy3→Cy3.5→Cy5]$_n$→Cy5.5 photonic wire and the 2:1, 3:1, and 4:1 0.5×$R_0$ dendrimer structures as compared to the initial 1.5×$R_0$ linear system. Note the break in vertical scale. FIG. 4B shows a comparison of the normalized emission profiles for the 0.5×$R_0$ 2:1 dendrimer and 8-arm photonic wire star structures. Dye ratios corresponding to each position in each structure are indicated with red or blue. Note the significant deconvolved Cy5.5 sensitization for the 2:1 dendrimer-inset. FIG. 4C is a comparative plot of the sensitized components at each step for the [Cy3→Cy3.5→Cy5]$_n$→Cy5.5 photonic wire system. Dye emissions are scaled and normalized to the highest component, the Cy3.5 sensitized emission in the 8-arm star structure. FIG. 4D is a comparative plot of the sensitized components at each step for the 0.5×$R_0$ 2:1, 3:1, and 4:1 dendrimer system. Dye emissions are scaled and normalized to the highest component, the Cy3.5 sensitized emission in the 4:1 structure.

FIGS. 5A-5D show comparisons of "ideal" simulations with experimental spectra for full 4-dye photonic wire structures with 1, 2, 4, and 8 arms at 0.5×, 1.0×, and 1.5×$R_0$, and for dendrimers with branching ratios of 2:1, 3:1, and 4:1 (0.5×$R_0$). These simulations show that multiple parallel interacting pathways are better than independent pathways. When photonic wire dye spacing is 1.5×$R_0$ (FIG. 5A), "ideal" simulations are seen to be in excellent agreement with data, which is not surprising given the weakness of the FRET. At 1.0×$R_0$ dye spacing (FIG. 5B) agreement is again good for Cy3 and Cy3.5 emission, but less so for the other dyes and especially Cy5.5. Finally, for dye spacings of 0.5×$R_0$, "ideal" simulations of both the photonic wires (FIG. 5C) and dendrimers (FIG. 5D) do not show a good march to the observed spectra.

Figure 6A:
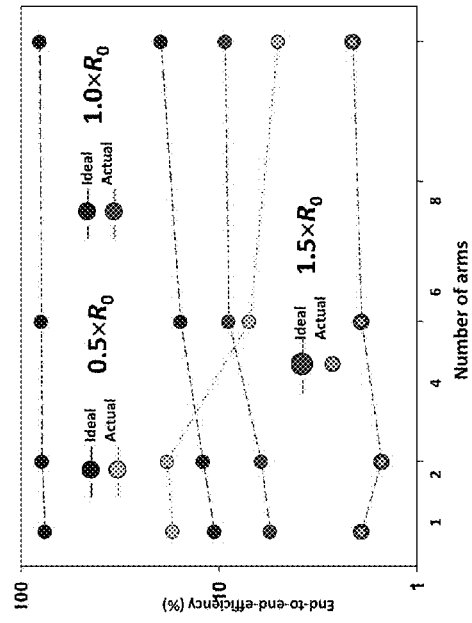
FIGS. 6A-6D show calculated ideal yield and efficiency.

For the "low-yield" modeling, the simulated ensembles were taken to be made up of target structure plus one or more partial structures, with all unincorporated dyes treated as "free." For simplicity, partial structures were restricted to having each dye in full complement but with fewer dye types present, approximating the composite contribution of a wide variety of potential non-fully-formed structures. With this approach, one obtains excellent agreement with experiment, and to interpret the results target structure yields derived in this way (with ¾ dyes) were compared to those estimated from gel electrophoresis in FIG. 6A. In general, yield characteristics for the photonic wire and dendrimer structures are similar and suggest a common failure mechanism. That the yields for the two-dye structures (not shown) and for the total (target+partial) product for all structures are uniformly high indicates that the Cy3 and Cy3.5 dyes assemble with high fidelity and that the observed "non-ideal" behavior is due entirely to the Cy5 and/or Cy5.5 dyes. Moreover, since simulated yields with 3- and 4-dyes are similar, Cy5 becomes the likely culprit since it must function properly for downstream Cy5.5 to do so. The decline of assembly yield with increased structural complexity, suggests a "crowding" effect due to either impaired hybridization and/or poor Cy5 properties/(self)quenching as noted before. That performance did not improve when Cy5 was replaced with AF647 in the 5-dye 2:1 dendrimer (FIG. 1D, FIG. 3G,H) may indicate an assembly problem.

Figure 6B:
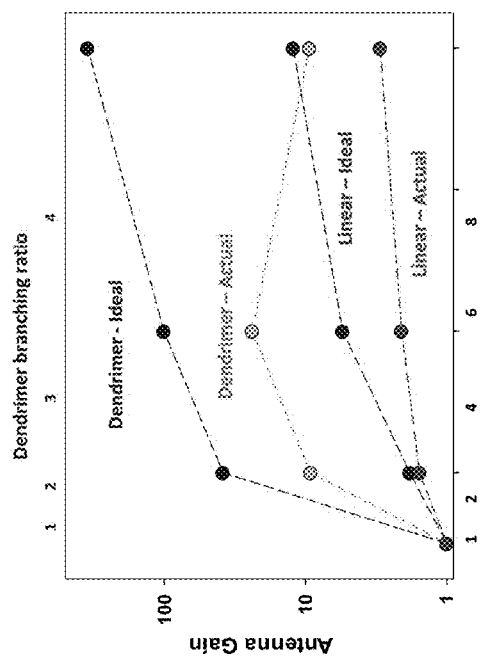
Figure 6C:
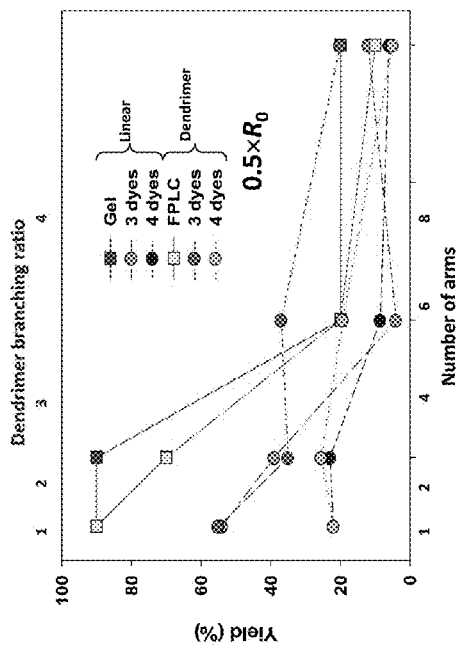
Figure 6D:
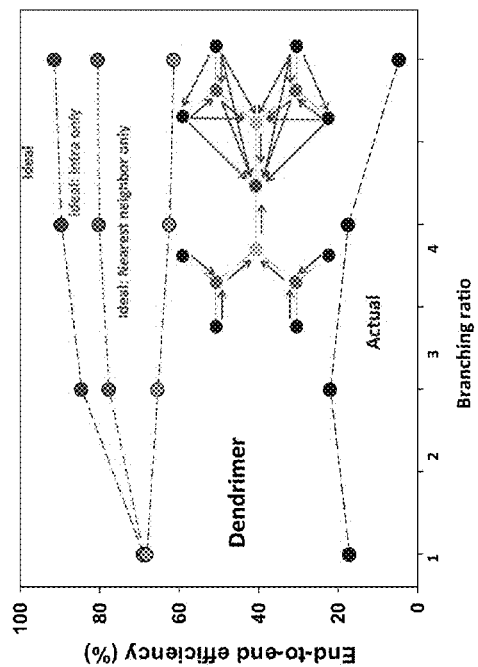
Figure 7A:
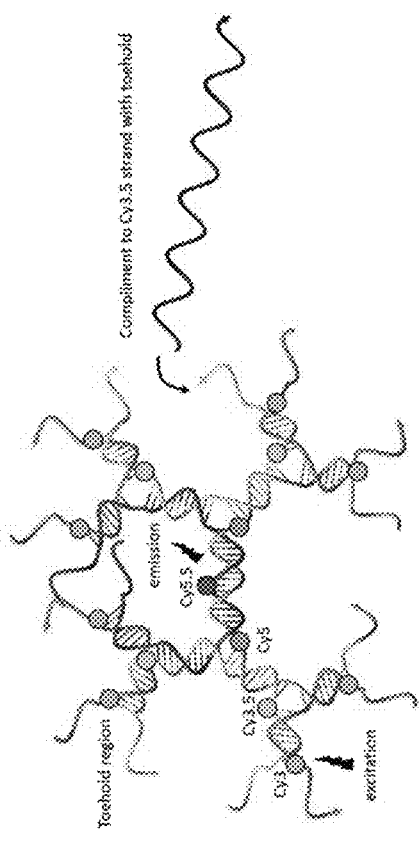
FIGS. 7A-7D schematically illustrate an exemplary dendrimer-based DNA sensor.
Figure 7B:
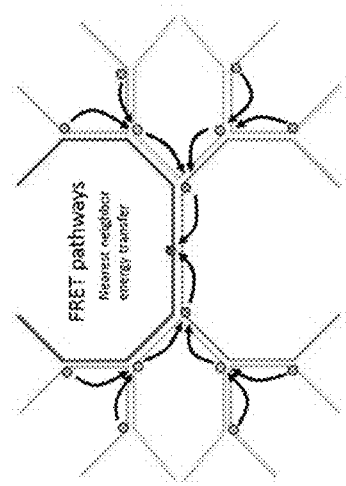
Figure 7C:
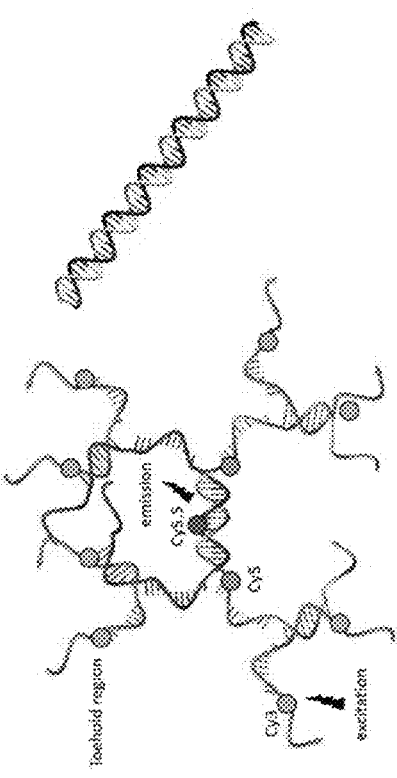
Figure 7D:
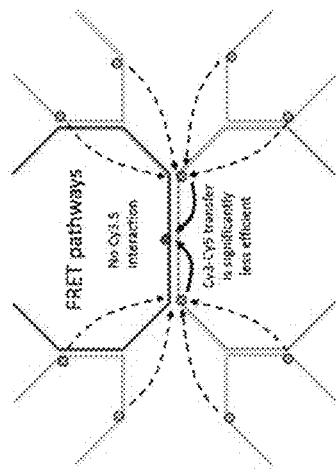

Presuming "low-yield" simulations constitute a plausible understanding of system photophysics, their actual and ideal efficiencies were estimated along with gain parameters. In FIG. 6B, E is plotted for four-dye wires as a function of arm number, with ideal results showing the expected strong boost in efficiency as dye spacing is reduced. That the ideal curves are relatively flat indicates that the arms act mostly independently supporting our previous conjecture. Actual efficiencies are greatly reduced in the 1.0× and 0.5×$R_0$ cases by the yield issues already discussed. End-to-end dendrimer efficiencies are shown in FIG. 6C with the low "actual" values again resulting from poor yield. In the ideal case, efficiency rises with increasing branching ratio by about 30%, although the 3:1/4:1 cases are not especially different. The reason for both the rise and saturation are the parallel paths in the structure. To investigate further, within FIG. 6C we show results from additional simulations in which FRET was variously restricted. When only nearest-neighbor dye couplings were included (inset, left side), no efficiency enhancements due to branching were observed. When couplings were instead restricted to only among dyes on the same branch (inset, right side), then a large fraction of the full ideal curve was realized. Thus, both intra- and inter-branch parallel paths contribute to efficiency enhancement making the dendrimers inherently more efficient than the photonic wire constructs where the arms act largely independently. The antenna properties using an antenna gain (AG) metric analogous to TEF but relative to the equivalent linear photonic wire (i.e., equal dye spacing) were also examined. Both "ideal" and "actual" AG for the four-dye photonic wire and dendrimer structures are plotted in FIG. 6D. The ideal curve for the wires is close to the unity slope expected if all arms operated independently; the slightly higher slope reflects a small contribution from parallel paths. Actual AG is much lower, again because of yield issues. For the dendrimers, there is potential for dramatic (exponential) increases in collection with the 4:1 structure ideally producing a gain of nearly 400. Yield again causes AG realized to be worse, with the 4:1 dendrimer AG exhibiting a decline.

The multiple interacting parallel FRET pathways as found in the dendrimer deliver more energy and thus more signal for any potential sensing versus multiple independent pathways as found in the linear and Holliday-star systems.

The following section on a sensor embodiment also includes exemplary sequences used to create a dendrimer scaffold.

Nanoscale Antenna as a Sensor

Including a "toehold" region in the nucleic scaffold allows for sensors operable on the basis of complementarity. FIGS. 7A-7D schematically illustrate an exemplary dendrimer-based DNA sensor. As can be seen, a portion of the scaffold incorporating an intermediate fluorophore (in this case, those elements incorporating Cy3.5) includes a toehold sequence that is not 100% hybridized with the other elements of the assembled scaffold via nucleic acid complementarity. Thus, upon contact with a sequence a high degree of complementary to the toehold sequence, this portion departs the scaffold (it can be washed away or may simply depart by diffusion), resulting in a measurable change in photophysical properties.

Although FIGS. 7A-7D illustrate only a single toehold sequence in the scaffold, namely on the elements containing the Cy3 dye, a single scaffold can have more than one distinct toehold sequence. For example, the exemplary sequences below have multiple toehold positions which could allow for a more pronounced change in response upon binding of a complement sequence. In embodiments with more than one scaffold element having a toehold sequence, the toehold sequences may be the same or different within a single scaffold The following sequences were used to create the nanoscale antenna depicted in FIGS. 7A-7D. In each case, the sequences AGGGAACGAA (SEQ ID No: 11) and AAGTGCATC (SEQ ID No: 12) are the toehold regions:

```
21den5s 36 (SEQ ID No: 13):
AGGGAACGAA/Cy3/AGAAGAGACAGGGAGT/Cy3/AAGTGCATC

21den5s 58 (SEQ ID No: 14):
AGGGAACGAACTCCCTGTT/Cy3.5/ACGACCCAGAAGTCACGGGAT/

Cy3.5/TCTCTTCTAATGTGCATC

21den5s 76A 2Cy5 (SEQ ID No: 15):
AGGGAACGAACTCCCTGTATCCCGTGAC/Cy5/TAACTCGTGAGTGCGGC A/Cy5/CTGGGTCGTATCTCTTCTAATGTGCATC 21den5s 76B Cy55 (SEQ ID No: 16):
AGGGAACGAACTCCCTGTATCCCGTGACTTGCCGCAC/Cy5.5/CACGAG

TTATCTGGGTCGTATCTCTTCTAATGTGCATC

21den5s 58 complementary sequence (SEQ ID No: 17):
GATGCACATTAGAAGAGAATCCCGTGACTTCTGGGTCGTAACAGGGAGTT

CGTTCCCT

21den5s 76A complementary sequence (SEQ ID No: 18):
GATGCACATTAGAAGAGATACGACCCAGATGCCGCACTCACGAGTTAAGTC

ACGGGATACAGGGAGTTCGTTCCCT
```

Figure 8A:
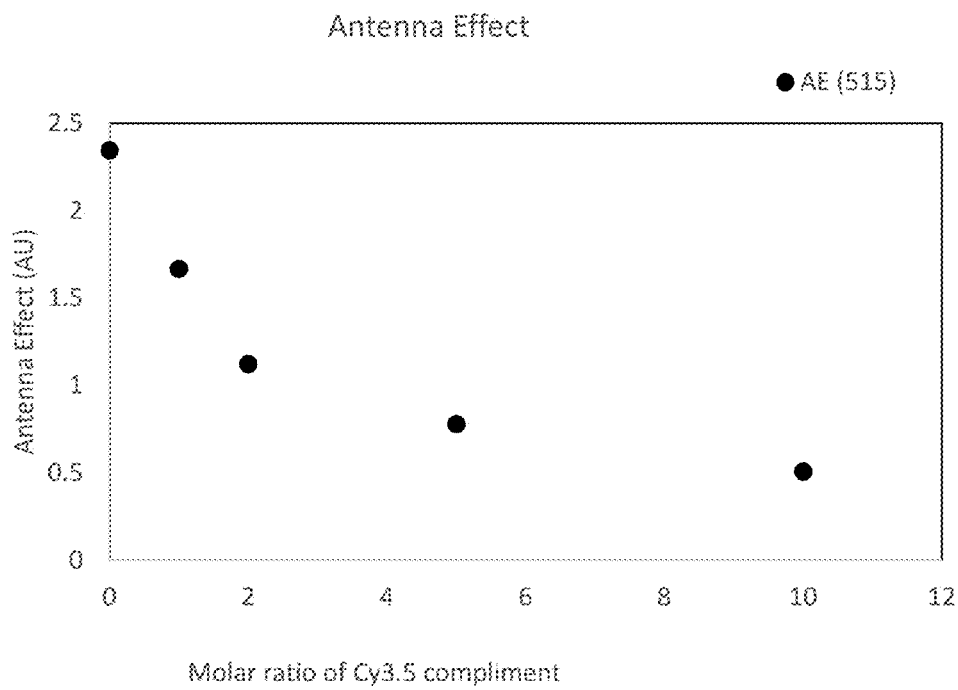
FIGS. 8A and 8B show representative photophysical characterization of some of the structures in FIGS. 7A-7D.
Figure 8B:
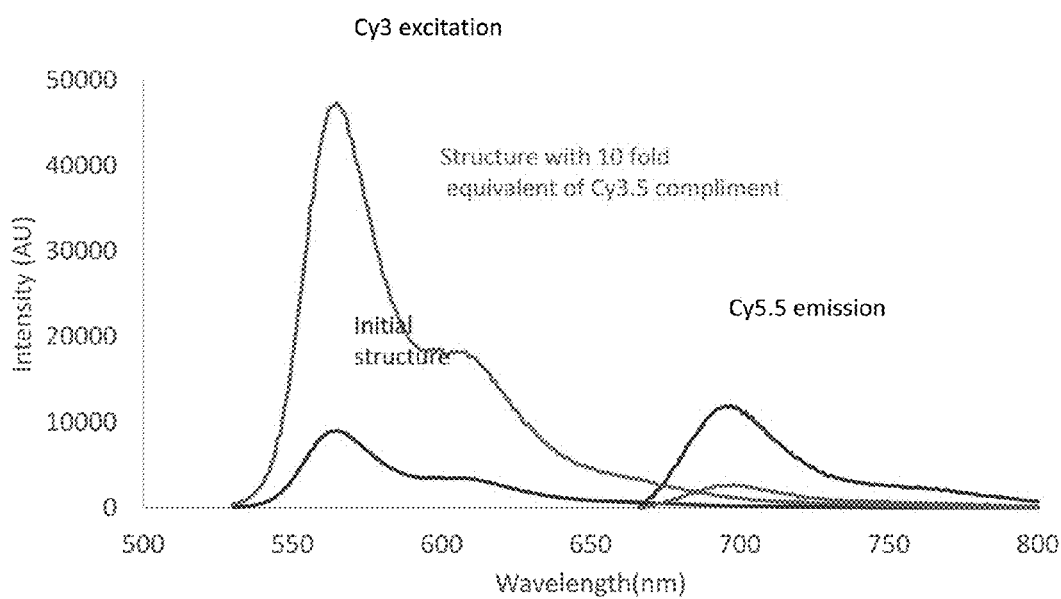

As seen in FIGS. 8A and 8B, the resulting amplification-like effect of the nanoscale antenna results in an enhanced signal with potential utility in sensor applications. Namely, by contacting such an antenna with an analyte and exciting the antenna, the degree of response of the antenna to the excitation can indicate a degree of presence in the analyte by the sequence complementary to the toehold sequence.

A sensor could include, for example, an array of such antennae, and optionally apparatus to excite and/or measure the response thereof.

Advantages

Techniques described herein use nucleic acid to pattern molecules capable of energy transfer at specified distances such that the energy transfer is controlled, enabling multi-step energy transfer with control over the discrete number of FRET steps. This allows for easy reconfiguration of the energy transfer network through the changing of: (a) number of molecules involved in each energy cascade; (b) the number of linear cascading branches that funnel to a single energy acceptor; and/or (c) the number of donor/acceptor molecules involved in each discrete energy transfer step. The modular design allows for multiple configurations within the same building set.

Nanoscale antennas as described herein can be used with other molecular donor/acceptor pairs beyond the fluorescent dyes used in the examples, for example quantum dots and/or other optically active materials. The scaffold can be built in two or three dimensions and have the flexibility to incorporate a wide range of dues or other fluorophores any in a highly controllable configuration.

The technique can involve multiple individual FRET pathways, multiple parallel pathways, or both, and can direct light energy inwards, outwards, or both, or alternatively, in a desired direction. One embodiment may have one or more terminal acceptors act as donors in FRET for a post-terminal acceptor, away from the central position.

A nanoscale antenna can incorporate multiple identical or different fluorophores at each step to augment energy flow.

Nanoscale antennas have the potential to allow longer range FRET interactions to compensate for deficiencies in structure or fluorophore function. They can harvest light energy one of a wide variety of wavelengths of choice, or at multiple wavelengths and have potential utility in optical coding, information storage, information processing, data encryption and sensitization for energy conversion. The techniques described herein also have utility as a research tool for studying light-harvesting (for example in synthetic mimics of photosynthesis).

Although the examples used DNA, the scaffold can incorporate many other nucleic acids and derivatives including RNA, PNA, LNA, etc. The nanoscale antennas can be easily integrated with other optically active materials such as, metal chelates, polymers, quantum dots or gold clusters, and furthermore can be designed to be responsive to change in temperature or ionic strength by changing its configuration or hybridization properties, this may also alter FRET properties.

The nanoscale antennas can be arranged on or incorporate active DNA structures that undergo functional rearrangements in response to external stimuli (e.g. another DNA or enzyme) which leads to a rearrangement or alteration in ET processes. Moreover, they can be used to create complex sensing devices such as those capable of detecting changes in pH (by configuring aspects of the antenna to respond to pH). They can incorporate photoactivatable groups that allow light stimulus to drive subsequent events such as a cleavage for drug delivery.

The nanoscale antennas are expected to have a high degree of biocompatibility and can be utilized for biological imaging with reduced background from direct excitation. They could function in a time-gated modality assuming insertion of appropriate fluorophores with requisite excited state lifetimes, and/or in direct excitation or multiphoton modalities.

The technique described herein allows for antennas that can be biochemically modified to allow site-specific conjugation to other biological or abiotic moieties of interest (e.g. a fluorescent protein or drug). Moreover, they can be site-specifically modified to allow (a) tethering of the entire structure to an electrode or desired surface (as in a sensor application), optionally through the use of specific binding peptides (e.g. polyhistidine, or polycysteine).

A further advantage is that, as implemented here, the technique utilizes a "one-pot" assembly strategy without requiring subsequent purification steps. It can be utilized in both ensemble mode or for single-molecule applications. Additionally, the nanoscale antennas can be assembled with or incorporate other types of DNA architectures besides the discrete structures utilized here such as DNA origami.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Teo, Y. N. & Kool, E. T. DNA-multichromophore systems. Chem. Rev. 112, 4221-4245 (2012)

Ohya, Y.; Yabuki, K.; Komatsu, M.; Ouchi, T. Polym. Adv. Technol. 2000, 11, 845

Ohya, Y.; Yabuki, K.; Hashimoto, M.; Nakajima, A.; Ouchi, T. Bioconjug. Chem. 2003, 14, 1057

Vyawahare, S.; Eyal, S.; Mathews, K. D.; Quake, S. R. Nano Lett. 2004, 4, 1035

Hannestad, J. K.; Sandin, P.; Albinsson, B. J. Am. Chem. Soc. 2008, 130, 15889

Wang, X.; Seeman, N. C., Assembly and Characterization of 8-arm and 12-arm DNA Branched Junctions. Journal of the American Chemical Society 2007, 129 (26), 8176.

Li, Y.; Tseng, Y. D.; Kwon, S. Y.; d'Espaux, L.; Bunch, J. S.; McEuen, P. L.; Luo, D., Controlled assembly of dendrimer-like DNA. Nature Materials 2004, 3 (1), 42.

Varghese R, Wagenknecht H A. DNA as a supramolecular framework for the helical arrangements of chromophores: towards photoactive DNA-based nanomaterials. Chem Commun 2009 May 21; (19):2615-24.

Dutta P K, Varghese R, Nangreave J, Lin S, Yan H, Liu Y. DNA-directed artificial light-harvesting antenna. J Am Chem Soc. 2011 Aug. 10; 133(31):11985-93.

Bo Albinsson, Jonas K. Hannestad, Karl Börjesson. Functionalized DNA nanostructures for light harvesting and charge separation. Coordination Chemistry Reviews. 256, 2012, 2399-2413.

Ziessel R, Ulrich G, Haefele A, Harriman A. An artificial light-harvesting array constructed from multiple Bodipy dyes. J Am Chem Soc. 2013 135:11330-44.

Rothemund Paul W. K., Methods of making nucleic acid nanostructures U.S. Pat. No. 7,842,793

Rothemund Paul W. K., Method for construction universal DNA based molecular Turing machine U.S. Pat. No. 5,843,661

TABLE I

Fluorophore photophysical and FRET properties.

| Fluorophores | QY | Ext. coeff. ($M^{-1}cm^{-1}$) | $\lambda_{max}$ abs. (nm) | $\lambda_{max}$ em. (nm) | $^1R_0$ in Å/J($\lambda$) in $cm^3M^{-1}$ | | | | | |
|---|---|---|---|---|---|---|---|---|---|---|
| | | | | | AF488 | Cy3 | Cy3.5 | Cy5 | AF647 | Cy5.5 |
| AF488 | 0.39 | 71,000 | 495 | 519 | 46/1.23e$^{-13}$ | 61/6.94e$^{-13}$ | 59/5.93e$^{-13}$ | 49/1.90e$^{-13}$ | 47/1.42e$^{-13}$ | 43/8.92e$^{-14}$ |
| Cy3 | 0.15 | 150,000 | 550 | 570 | — | 47/3.68e$^{-13}$ | 53/8.01e$^{-13}$ | 54/9.37e$^{-13}$ | 53/7.83e$^{-13}$ | 49/4.73e$^{-13}$ |
| Cy3.5 | 0.15 | 150,000 | 581 | 596 | — | — | 44/2.70e$^{-13}$ | 60/1.69e$^{-12}$ | 59/1.58e$^{-12}$ | 55/1.01e$^{-12}$ |
| Cy5 | 0.28 | 250,000 | 649 | 670 | — | — | — | 65/1.39e$^{-12}$ | — | 68/1.94e$^{-12}$ |
| AF647 | 0.33 | 239,000 | 650 | 665 | — | — | — | — | 65/1.17e$^{-12}$ | 72/2.18e$^{-12}$ |
| Cy5.5 | 0.23 | 190,000 | 675 | 694 | — | — | — | — | — | 63/1.41e$^{-12}$ |

$^1R_0$ and J($\lambda$) values are averages calculated from the spectra of all dye-labeled DNA used in this study.
QY—quantum yield.

TABLE 2

Antenna effect (AE) and end-to-end efficiency (E) for the Cy3-Cy5 single FRET step system.

| | | | Förster distance/donor-acceptor separation | | | | |
|---|---|---|---|---|---|---|---|
| Construct | (#Cy3/Cy5) | $\varepsilon_{Cy3n}/\varepsilon_{Cy5}$$^1$ | 0.75/40.5 Å AE (%)/E (%) | 0.85/45.9 Å AE/E | 1.0/54 Å AE/E | 1.25/67.9 Å AE/E | 1.5/81 Å AE/E |
| Linear | (1) | 0.6 | 108/40 | 76/22 | 54/18 | 34/9 | 16/3 |
| Bifurcated | (2) | 1.2 | 185/51 | 128/28 | 84/20 | 55/10 | 30/4 |
| Holliday junction | (4) | 2.4 | 291/37 | 120/30 | 144/23 | 83/9 | 31/4 |
| 8-arm star | (8) | 4.8 | 252/15 | 163/16 | 183/15 | 80/8 | 46/2 |

All values are collected from at least 3 independently assembled structures. Standard deviations for AE and E values are all <10%.
$^1$Initial Cy3$_n$ absorption at 550 nm relative to the final Cy5 absorption at 650 nm.

TABLE 3

Antenna effect (AE) and end-to-end efficiency (E) for the 4/5-dye photonic wire and dendrimer systems.

| | | | Förster distance | | |
|---|---|---|---|---|---|
| Construct | (#wires$^3$/Cy5.5) | $\varepsilon_{Cy3n}/\varepsilon_{Cy5.5}$$^4$ | 0.5 × $R_0$$^{1,2}$ AE (%)/E (%) | 1.0 × $R_0$ AE (%)/E (%) | 1.5 × $R_0$ AE (%)/E (%) |
| Linear | 1 | 0.8 | 184/16 | 46/4 | 17/2 |
| Bifurcated | 2 | 1.6 | 285/14 | 85/7 | 13/1 |

TABLE 3-continued

Antenna effect (AE) and end-to-end efficiency (E) for the 4/5-dye photonic wire and dendrimer systems.

| | | | | | |
|---|---|---|---|---|---|
| Holliday junction | 4 | 3.2 | 107/9 | 73/9 | 21/3 |
| 8-arm star | 8 | 6.3 | 113/6 | 78/6 | 34/2 |
| 4-dye | (#Cy3/Cy5.5) | | | | |
| 2:1 dendrimer | 8 | 6.3 | 217/17 | — | — |
| 3:1 dendrimer | 27 | 21.3 | 393/23 | — | — |
| 4:1 dendrimer | 64 | 50.5 | 158/8 | — | — |
| 5-dye dendrimer | (#AF488/Cy5.5) | $\varepsilon AF488n/\varepsilon Cy5.55$ | | | |
| 2:1 (Cy5)[6] | 16 | 6 | 180/19 | — | — |
| 2:1(AF647)[6] | 16 | 6 | 140/16 | — | — |

All values were collected from at least 3 independently assembled structures.
Standard deviations for AE and E values are all <10%.
[1]See Table 1 for individual dye-dye $R_0$ values.
[2]Standard deviations of all values <10%.
[3]Wire = $[Cy3\rightarrow Cy3.5\rightarrow Cy5]_n$.
[4]Initial $Cy3_n$ absorption at 550 nm relative to the final Cy5.5 absorption at 700 nm.
[5]Initial $AF488_n$ absorption at 550 nm relative to the final Cy5.5 absorption at 700 nm.
[6]Displaying either Cy5 or AF647 at the 4$^{th}$ dye.

What is claimed is:

1. A nanoscale antenna comprising:
a nucleic acid scaffold having a structure selected from the group consisting of a Holliday junction, a star, and a dendrimer; and
a plurality of fluorophores attached to the scaffold and configured as a FRET cascade comprising at least three different types of fluorophores, arranged with (a) a plurality of initial donor fluorophores fixed in exterior positions on the structure, (b) a terminal acceptor fluorophore fixed in a central position on the structure, and (c) a plurality of intermediate fluorophores fixed in positions on the scaffold between the initial acceptor fluorophores and the terminal acceptor fluorophore,
wherein one or more portions of said scaffold incorporating intermediate fluorophores further comprise a toehold sequence, and are detachable from said scaffold upon contact with a sequence complementary to the toehold sequence, and
wherein the plurality of fluorophores comprises at least one form of quantum dot.

2. The nanoscale antenna of claim 1, wherein said nucleic acid is DNA and wherein at least one of the fluorophores is a fluorescent dye integrated into the DNA via phosphoramidite chemistry; succinimidyl ester chemistry; maleimide thiol chemistry; a carboxyl-amine amide bond; azide-alkyne cycloaddition; or a combination thereof.

3. The nanoscale antenna of claim 1, wherein said FRET cascade includes a total of 3, 4, 5, or 6 different types of fluorophores.

4. The nanoscale antenna of claim 1, wherein said terminal acceptor comprises one or more fluorophores configured donors in FRET for a post-terminal flurophore acceptor located away from said central position.

5. A nanoscale antenna comprising:
a nucleic acid scaffold having a dendrimer structure, and
a plurality of fluorophores attached to the scaffold and configured as a FRET cascade comprising at least three different types of fluorophores, arranged with (a) a plurality of initial donor fluorophores fixed in exterior positions on the structure, (b) a terminal acceptor fluorophore fixed in a central position on the structure, and (c) a plurality of intermediate fluorophores fixed in positions on the scaffold between the initial acceptor fluorophores and the terminal acceptor fluorophore,
wherein one or more portions of said scaffold incorporating intermediate fluorophores further comprise a toehold sequence, and are detachable from said scaffold upon contact with a sequence complementary to the toehold sequence, and
wherein the plurality of fluorophores comprises at least one form of quantum dot.

6. The nanoscale antenna of claim 5, wherein said nucleic acid is DNA and wherein at least one of the fluorophores is a fluorescent dye integrated into the DNA via phosphoramidite chemistry; succinimidyl ester chemistry; maleimide thiol chemistry; a carboxyl-amine amide bond; azide-alkyne cycloaddition; or a combination thereof.

7. The nanoscale antenna of claim 5, wherein said FRET cascade includes a total of 3, 4, 5, or 6 different types of fluorophores.

8. The nanoscale antenna of claim 5, wherein said terminal acceptor comprises one or more fluorophores configured donors in FRET for a post-terminal flurophore acceptor located away from said central position.

9. A method of using a nanoscale antenna, the method comprising:
providing a nanoscale antenna comprising: a nucleic acid scaffold having a structure selected from the group consisting of a Holliday junction, a star, and a dendrimer; and a plurality of fluorophores attached to the scaffold and configured as a FRET cascade comprising at least three different types of fluorophores, arranged with (a) a plurality of initial donor fluorophores fixed in exterior positions on the structure, (b) a terminal acceptor fluorophore fixed in a central position on the structure, and (c) a plurality of intermediate fluorophores fixed in positions on the scaffold between the initial acceptor fluorophores and the terminal acceptor fluorophore, wherein the plurality of fluorophores comprises at least one form of quantum dot and wherein one or more portions of the scaffold incorporating intermediate fluorophores further comprise a toehold sequence detachable from said scaffold upon contact with a sequence complementary to the toehold sequence;
contacting the nanoscale antenna with an analyte;
exciting the antenna with a light source to excite the FRET cascade; and
measuring a response of said nanoscale antenna following the excitation, wherein the response indicates a degree of presence in the analyte of the sequence complementary to the toehold sequence.

10. The method of claim 9, wherein said nucleic acid is DNA and wherein at least one of the fluorophores is a fluorescent dye integrated into the DNA via phosphoramidite chemistry; succinimidyl ester chemistry; maleimide thiol chemistry; a carboxyl-amine amide bond; azide-alkyne cycloaddition; or a combination thereof.

11. The method of claim 9, wherein said FRET cascade includes a total of 3, 4, 5, or 6 different types of fluorophores.

* * * * *

SEQUENCE LISTING

```
<160> NUMBER OF SEQ ID NOS: 18

<210> SEQ ID NO 1
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Cy3 dye
<220> FEATURE:
<221> NAME/KEY: misc_feature
<222> LOCATION: (48)..(48)
<223> OTHER INFORMATION: Cy3 dye

<400> SEQUENCE: 1
ggagagatgg ttcagccgca atcctcgcct gcactctacc tgacttcc           48

<210> SEQ ID NO 2
<211> LENGTH: 47
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (25)..(25)
<223> OTHER INFORMATION: Cy5 dye

<400> SEQUENCE: 2
ggaagtcagg tagagtgcag gcgagagcac gagtcttgct gcttagc            47

<210> SEQ ID NO 3
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
```

<223> OTHER INFORMATION: Cy3 dye
<220> FEATURE:
<221> NAME/KEY: misc_feature
<222> LOCATION: (48)..(48)
<223> OTHER INFORMATION: Cy3 dye

<400> SEQUENCE: 3
gctaagcagc aagactcgtg ctcaccgaat gccaccacgc tccgtcgc                    48

<210> SEQ ID NO 4
<211> LENGTH: 48
<212> TYPE: DNA
<213> ORGANISM: Artificial Sequence
<220> FEATURE:
<223> OTHER INFORMATION: synthetic construct

<400> SEQUENCE: 4
gcgacggagc gtggtggcat tcggcgtcca gctctgatcc aatactcc                    48

<210> SEQ ID NO 5
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Cy3 dye
<220> FEATURE:
<221> NAME/KEY: misc_feature
<222> LOCATION: (48)..(48)
<223> OTHER INFORMATION: Cy3 dye

<400> SEQUENCE: 5
ggagtattgg atcagagctg gacgacaatg acgtaggtcc taacctcc                    48

<210> SEQ ID NO 6
<211> LENGTH: 48
<212> TYPE: DNA
<213> ORGANISM: Artificial Sequence
<220> FEATURE:
<223> OTHER INFORMATION: synthetic construct

<400> SEQUENCE: 6
ggaggttagg acctacgtca ttgtactatg gcacacatcc ctagttcc                    48

<210> SEQ ID NO 7
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: Cy3 dye
<220> FEATURE:
<221> NAME/KEY: misc_feature
<222> LOCATION: (48)..(48)
<223> OTHER INFORMATION: Cy3 dye

<400> SEQUENCE: 7
ggaactaggg atgtgtgcca tagtggtcaa cgcatacacc ttctatcc                    48

<210> SEQ ID NO 8
<211> LENGTH: 48
<212> TYPE: DNA
<213> ORGANISM: Artificial Sequence

```
<220> FEATURE:
<223> OTHER INFORMATION: synthetic construct

<400> SEQUENCE: 8
ggatagaagg tgtatgcgtt gaccggattg cggctgaacc atctctcc          48

<210> SEQ ID NO 9
<211> LENGTH: 48
<212> TYPE: DNA
<213> ORGANISM: Artificial Sequence
<220> FEATURE:
<223> OTHER INFORMATION: synthetic construct

<400> SEQUENCE: 9
gcgacggagc gtggtggcat tcggggattg cggctgaacc atctctcc          48

<210> SEQ ID NO 10
<211> LENGTH: 47
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (24)..(24)
<223> OTHER INFORMATION: Cy5 dye

<400> SEQUENCE: 10
ggaggttagg acctacgtca ttgcgtccag ctctgatcca atactcc           47

<210> SEQ ID NO 11
<211> LENGTH: 10
<212> TYPE: DNA
<213> ORGANISM: Artificial Sequence
<220> FEATURE:
<223> OTHER INFORMATION: synthetic construct

<400> SEQUENCE: 11
agggaacgaa                                                    10

<210> SEQ ID NO 12
<211> LENGTH: 9
<212> TYPE: DNA
<213> ORGANISM: Artificial Sequence
<220> FEATURE:
<223> OTHER INFORMATION: synthetic construct

<400> SEQUENCE: 12 aagtgcatc                                                      9

<210> SEQ ID NO 13
<211> LENGTH: 35
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (11)..(11)
<223> OTHER INFORMATION: Cy3 dye
<220> FEATURE:
<221> NAME/KEY: misc_feature
<222> LOCATION: (27)..(27)
<223> OTHER INFORMATION: Cy3 dye

<400> SEQUENCE: 13
agggaacgaa agaagagaca gggagtaagt gcatc                        35
```

```
<210> SEQ ID NO 14
<211> LENGTH: 58
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (20)..(20)
<223> OTHER INFORMATION: Cy3.5 dye
<220> FEATURE:
<221> NAME/KEY: misc_feature
<222> LOCATION: (41)..(41)
<223> OTHER INFORMATION: Cy3.5 dye

<400> SEQUENCE: 14
agggaacgaa ctccctgtta cgacccagaa gtcacgggat tctcttctaa tgtgcatc      58

<210> SEQ ID NO 15
<211> LENGTH: 74
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (29)..(29)
<223> OTHER INFORMATION: Cy5 dye
<220> FEATURE:
<221> NAME/KEY: misc_feature
<222> LOCATION: (47)..(47)
<223> OTHER INFORMATION: Cy5 dye

<400> SEQUENCE: 15
agggaacgaa ctccctgtat cccgtgacta actcgtgagt gcggcactgg gtcgtatctc    60
ttctaatgtg catc                                                      74

<210> SEQ ID NO 16
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (38)..(38)
<223> OTHER INFORMATION: Cy5.5 dye

<400> SEQUENCE: 16
agggaacgaa ctccctgtat cccgtgactt gccgcaccac gagttatctg ggtcgtatct    60
cttctaatgt gcatc                                                     75

<210> SEQ ID NO 17
<211> LENGTH: 58
<212> TYPE: DNA
<213> ORGANISM: Artificial Sequence
<220> FEATURE:
<223> OTHER INFORMATION: synthetic construct

<400> SEQUENCE: 17
gatgcacatt agaagagaat cccgtgactt ctgggtcgta acaggagtt cgttccct       58

<210> SEQ ID NO 18
<211> LENGTH: 76
<212> TYPE: DNA
<213> ORGANISM: Artificial Sequence
<220> FEATURE:
<223> OTHER INFORMATION: synthetic construct
```

```
<400> SEQUENCE: 18
gatgcacatt agaagagata cgacccagat gccgcactca cgagttaagt cacgggatac      60
agggagttcg ttccct                                                     76
```